US012383583B2

United States Patent
Tanabe et al.

(10) Patent No.: US 12,383,583 B2
(45) Date of Patent: Aug. 12, 2025

(54) PHARMACEUTICAL COMPOSITION AND COSMETIC COMPOSITION

(71) Applicants: Koji Tanabe, Palo Alto, CA (US); I Peace, Inc., Palo Alto, CA (US)

(72) Inventors: Koji Tanabe, Palo Alto, CA (US); Kenta Suto, Palo Alto, CA (US)

(73) Assignee: I Peace, Inc., Palo Alto, CA (US)

( * ) Notice: Subject to any disclaimer, the term of this patent is extended or adjusted under 35 U.S.C. 154(b) by 0 days.

(21) Appl. No.: 18/734,602

(22) Filed: Jun. 5, 2024

(65) Prior Publication Data

US 2024/0316117 A1  Sep. 26, 2024

Related U.S. Application Data

(62) Division of application No. 17/292,298, filed as application No. PCT/JP2019/039396 on Oct. 4, 2019, now Pat. No. 12,036,245.

(60) Provisional application No. 62/756,780, filed on Nov. 7, 2018.

(51) Int. Cl.
| | |
|---|---|
| *A61K 35/545* | (2015.01) |
| *A61K 8/98* | (2006.01) |
| *A61P 17/14* | (2006.01) |
| *A61Q 19/08* | (2006.01) |

(52) U.S. Cl.
CPC ............ *A61K 35/545* (2013.01); *A61K 8/982* (2013.01); *A61P 17/14* (2018.01); *A61Q 19/08* (2013.01)

(58) Field of Classification Search
CPC ................................ A61P 17/02; A61Q 19/08
See application file for complete search history.

(56) References Cited

U.S. PATENT DOCUMENTS

| | | |
|---|---|---|
| 2007/0087437 A1 | 4/2007 | Hu |
| 2009/0068742 A1 | 3/2009 | Yamanaka |
| 2010/0120042 A1 | 5/2010 | Noh et al. |
| 2016/0081913 A1 | 3/2016 | Hong et al. |
| 2018/0305671 A1 | 10/2018 | Koehler et al. |
| 2019/0330594 A1 | 10/2019 | You et al. |

FOREIGN PATENT DOCUMENTS

| | | |
|---|---|---|
| CN | 103784474 A | 5/2014 |
| CN | 104324053 A | 2/2015 |
| CN | 104762260 A | 7/2015 |
| CN | 106109496 A | 11/2016 |
| CN | 107158165 A | 9/2017 |
| JP | 4183742 B1 | 11/2008 |
| JP | 2009-526517 A | 7/2009 |
| JP | 2012508006 A | 4/2012 |
| JP | 2016-516811 A | 6/2016 |
| JP | 2016-128396 A | 7/2016 |
| JP | 2017-104085 A | 6/2017 |
| JP | 2018-531027 A | 10/2018 |
| KR | 10-2013-0109999 A | 10/2013 |
| WO | 2010141801 A2 | 12/2010 |
| WO | WO-2010138517 A1 * | 12/2010 ........... C12N 5/0696 |
| WO | 2013134513 A1 | 9/2013 |
| WO | 2018/131900 A2 | 7/2018 |

OTHER PUBLICATIONS

Kang J et al, "Effects of Reprogramming-Conditioned Medium on Ultraviolet Ray A-Damaged Human Dermal Fibroblasts", Preproduction, Fertility and Development, Dec. 2, 2016, vol. 29, No. 1, p. 208.
Kenzo Takahashi, "Molecular Biology Concerning Hair Development, Toward Regeneration of Lost Hair", Medical Practice, 1999, vol. 16, No. 10, p. 1688-1689.
Hajime Iizuka et al, "Growth Control of Epidermal Cells in Wound Healing", 1996, vol. 38, No. 1, p. 132-147.
Tatsuya Matsui et al, "Effects of Prostaglandin on VEGF Production from Cultured Human Dermal Fibroblasts", St. Marianna University School of Medicine Magazine, 2003, vol. 31, p. 123-130.
Hajime Ikehara, "Gene Therapy and Personalized Medicine Using Disease Specific iPS Cells", Pediatrics of Japan, 2018, vol. 59, No. 12, p. 1777-1783.
Chikako Nishikiori, "Elucidation of Pathological Conditions and Development of Therapeutic Methods Using iPS Cells for Xeroderma Pigmentosum", 2014(Heisei 26) Progress Report from Entrusted Business, 2015, p. 15.
Kayoko Matsunaga, "Skin Care for Childhood Atopic Dermatitis", Journal of Pediatric Dermatology, 2004, vol. 23, No. 1, p. 310.
Masatoshi Ito et al, "Evaluation of Usefulness of BU Moisturizing Cream for Dry Skin and Xeroderma in Patients with Atopic Dermatitis", Skin Research, 2008, vol. 7, No. 4, p. 466-474.
Tsukahara H et al., "Oxidative Stress and Altered Antioxidant Defenses in Children With Acute Exacerbation of Atopic Dermatitis", Life Sciences, 2003, vol. 72, p. 2509-2516.
Uysal P. et al., "Association of Oxidative Stress and Dynamic Thiol-Disulphide Homeostasis with Atopic Dermatitis Severity and Chronicity in Children: A Prospective Study", Clinical and Experimental Dermatology, 2018, vol. 43, No. 2, p. 124-130.
Hayashi Y. et al, "Reduction of N-glycolylneuraminic Acid in Human Induced Pluripotent Stem Cells Generated or Culture under Feeder- and Serum-Free Defined Conditions", PLoS one, 2010, vol. 5, No. 11, e14099, pp. 1-11.
Beers J. et al., "A cost-effective and efficient reprogramming platform for largescale production of integration-free human induced pluripotent stem cells in chemically defined culture", Scientific Reports, 2015, 5:11319, pp. 19.
Sommer CA. et al., "Induced Pluripotent Stem Cell Generation Using a Single Lentiviral Stem Cell Cassette", Stem Cells, 2009, vol. 27, pp. 543-549.
Loretelli C. et al, "Embryonic Cell Extracts Ameliorate Wound Healing in Diabetic Mice", Diabetes, 2018, vol. 67, Suppl. 1, p. A330, 1231P.

(Continued)

*Primary Examiner* — Qiuwen Mi
(74) *Attorney, Agent, or Firm* — Studebaker Brackett PLLC

(57) ABSTRACT

Provided are a pharmaceutical composition or a pharmaceutical composition raw material, which contains supernatant from a culture medium used during culture to induce pluripotent stem cells.

13 Claims, 16 Drawing Sheets

(56) References Cited

OTHER PUBLICATIONS

Hashizume, Hideo; "Skin Aging and Dry Skin"; The Journal of Dermatology; vol. 31; Aug. 2004; pp. 603-609.

* cited by examiner

Bar = mean value ± SE, n=4

| SAMPLE | NEGATIVE CONTROL | CELL EXTRACT LIQUID | |
|---|---|---|---|
| | | 100% | 50% |
| COLLAGEN CONCENTRATION(ng/ml) n=4 | 1.46 | 2.47 | 2.71 |
| | 1.61 | 2.34 | 2.81 |
| | 1.34 | 2.40 | 2.58 |
| | 1.47 | 2.43 | 2.52 |
| MEAN | 1.47 | 2.41 | 2.65 |
| STANDARD ERROR | 0.04 | 0.02 | 0.05 |
| SIGNIFICANCE | REFERENCE | P<0.001 | P<0.001 |
| P VALUE | | 4.76E-06 | 9.13E-06 |

| SAMPLE | NEGATIVE CONTROL | CELL EXTRACT LIQUID | |
|---|---|---|---|
| | | 100% | 50% |
| wst-8 ABSORBANCE(OD450) n=3 | 0.802 | 1.088 | 1.007 |
| | 0.782 | 1.041 | 0.953 |
| | 0.806 | 0.961 | 0.966 |
| MEAN | 0.80 | 1.03 | 0.98 |
| STANDARD ERROR | 0.00 | 0.02 | 0.01 |
| SIGNIFICANCE | REFERENCE | P<0.01 | P<0.001 |
| P VALUE | | 0.003593 | 0.000545 |

Fig.7

| SAMPLE | NEGATIVE CONTROL | MINOXIDIL | ADDITION OF SUPERNATANT FROM INDUCTION CULTURE | | | CELL EXTRACT LIQUID | | DMSO | ADENOSINE |
|---|---|---|---|---|---|---|---|---|---|
| | | | 20% | 10% | 100% | 50% | | | |
| VEGF(pg/ml) n=3 | 215.7 | 273.0 | 566.5 | 414.9 | 1158.8 | 785.2 | 238.2 | 251.6 |
| | 209.6 | 249.9 | 588.7 | 425.4 | 1071.0 | 716.7 | 237.5 | 271.4 |
| | 244.5 | 259.2 | 631.6 | 467.5 | 1096.8 | 769.2 | 242.7 | 284.2 |
| MEAN | 223.2 | 260.7 | 595.6 | 435.9 | 1108.9 | 757.0 | 239.4 | 269.0 |
| STANDARD ERROR | 6.8 | 4.2 | 12.1 | 10.2 | 16.5 | 13.1 | 1.0 | 6.0 |
| SIGNIFICANCE | REFERENCE | P<0.05 | P<0.001 | P<0.001 | P<0.001 | P<0.001 | REFERENCE | P<0.05 |
| P VALUE | | 0.041938 | 7.05E-05 | 0.000389 | 6.12E-06 | 2.16E-05 | | 0.037001 |

Fig.9

| SAMPLE | NEGATIVE CONTROL | MINOXIDIL | ADDITION OF SUPERNATANT FROM INDUCTION CULTURE | | | CELL EXTRACT LIQUID | | DMSO | ADENOSINE |
|---|---|---|---|---|---|---|---|---|---|
| | | | 20% | 10% | 100% | 50% | | | |
| FGF-7(pg/ml) n=3 | 1.74 | 2.75 | 4.42 | 3.81 | 10.92 | 6.79 | 1.74 | 2.05 |
| | 4.20 | 2.77 | 5.10 | 3.68 | 11.63 | 6.51 | 1.73 | 2.04 |
| | 3.33 | 3.81 | 4.65 | 3.62 | 11.30 | 6.21 | 7.85 | 2.19 |
| MEAN | 3.09 | 2.77 | 4.72 | 3.70 | 11.29 | 6.50 | 1.77 | 2.10 |
| STANDARD ERROR | 0.46 | 0.01 | 0.13 | 0.04 | 0.13 | 0.11 | 0.02 | 0.03 |
| SIGNIFICANCE | REFERENCE | n.s. | n.s. | n.s. | P<0.001 | P<0.01 | REFERENCE | P<0.01 |
| P VALUE | | 0.685723 | 0.093899 | 0.443135 | 0.000396 | 0.009904 | | 0.00615 |

Fig.16
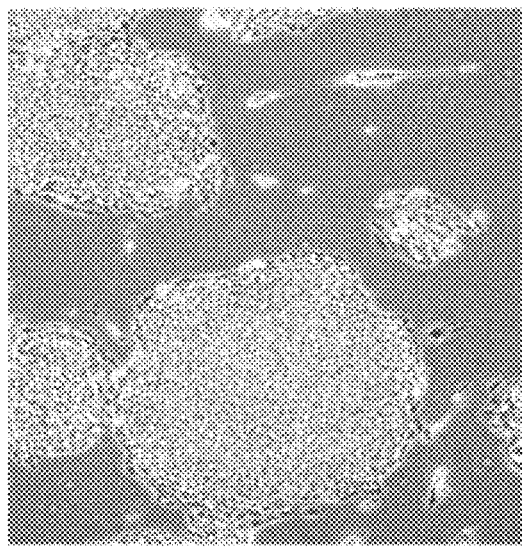
(b)
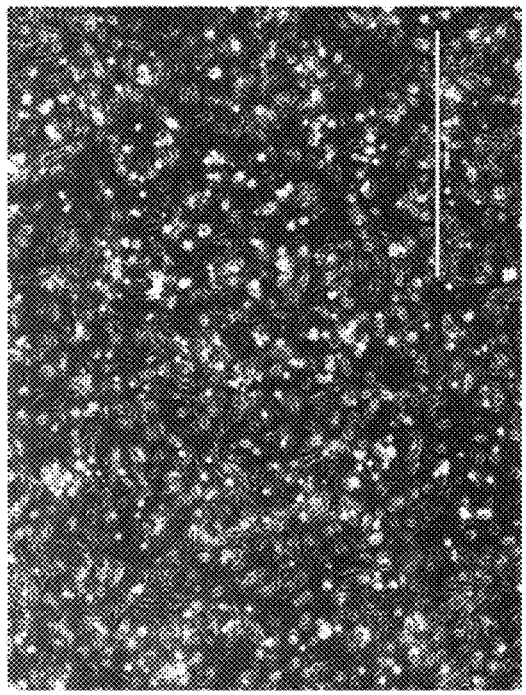
(a)

Fig. 17
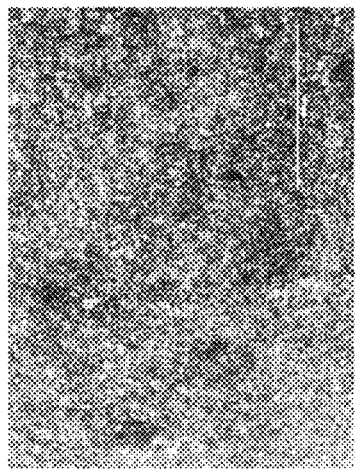
(c)
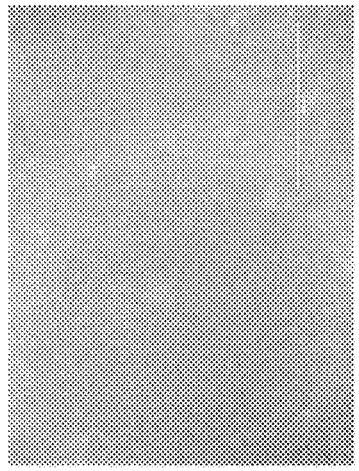
(b)
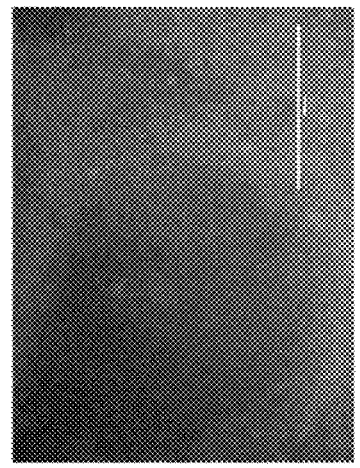
(a)

PHARMACEUTICAL COMPOSITION AND COSMETIC COMPOSITION

CROSS-REFERENCE TO RELATED APPLICATIONS

This application is a Divisional of U.S. patent application Ser. No. 17/292,298, filed May 7, 2021, which is the U.S. National Stage of International Application No. PCT/JP2019/039396, filed Oct. 4, 2019, and which claims the benefit of priority to U.S. Provisional Patent Application No. 62/756,780, filed Nov. 7, 2018, the entire contents of which are incorporated herein by reference.

TECHNICAL FIELD

The present invention relates to a pharmaceutical composition and to a cosmetic composition.

BACKGROUND ART

Embryonic stem cells (ES cells) are stem cells established from early embryos of mouse or human. ES cells exhibit a pluripotency that enables differentiation into any of the cells present in an organism. At present, human ES cells can be used in cell transplantation therapy for a number of diseases including Parkinson's disease, juvenile onset diabetes, and leukemia. However, there are barriers to ES cell transplantation. In particular, ES cell transplantation can induce an immunorejection similar to the rejection that occurs following unsuccessful organ transplantation. The use of ES cells that have been established by the destruction of human embryos has also received much criticism and opposition from an ethical standpoint.

With these circumstances as background, Professor Shinya Yamanaka of Kyoto University succeeded in establishing induced pluripotent stem cells (iPS cells) by the introduction of the four genes OCT3/4, KLF4, c-MYC, and SOX2 into somatic cells. Professor Yamanaka received the Nobel Prize in Physiology or Medicine in 2012 as a result (see, for example, Patent Document 1). iPS cells are ideal pluripotent cells which are free of rejection reactions and ethical issues. iPS cells are therefore considered promising for use in cell transplantation therapy. The reutilization, in pharmaceutical compositions, of culture medium that has been used to culture iPS cells has been reported (see, for example, Patent Document 2).

CITATION LIST

Patent Documents

Patent Document 1: Japanese Patent No. 4,183,742
Patent Document 2: Patent Publication JP-A-2016-128396

SUMMARY

Technical Problem

However, the present inventors confirmed that the iPS cells in the culture method described in Patent Document 2 ended up undergoing differentiation, and it is thus thought that the culture medium being reutilized is one in which differentiated cells were actually cultured, rather than iPS cells. An object of the present invention is to provide a pharmaceutical composition and a cosmetic composition that effectively utilize the culture medium from iPS cells.

Solution to Problem

According to an aspect of the present invention, a pharmaceutical composition or a pharmaceutical composition raw material containing a supernatant of a culture medium used during a reprogramming of somatic cells is provided.

According to an aspect of the present invention, an agent for preventing or ameliorating formation of any of skin blemishes, skin wrinkles, and skin sagging containing the aforementioned pharmaceutical composition or pharmaceutical composition raw material is provided.

According to an aspect of the present invention, a cosmetic composition or a cosmetic composition raw material containing a supernatant of a culture medium used during a reprogramming of somatic cells is provided.

According to an aspect of the present invention, an agent for preventing or ameliorating formation of any of skin blemishes, skin wrinkles, and skin sagging containing the aforementioned cosmetic composition or cosmetic composition raw material is provided.

According to an aspect of the present invention, a collagen production promoter or a collagen production promoter raw material containing a supernatant of a culture medium used during a reprogramming of somatic cells is provided.

According to an aspect of the present invention, a hair growth agent, hair growth agent raw material, hair restoration agent, or hair restoration agent raw material containing a supernatant of a culture medium used during a reprogramming of somatic cells is provided.

According to an aspect of the present invention, a hair papilla cell activator or a hair papilla cell activator raw material containing a supernatant of a culture medium used during a reprogramming of somatic cells is provided.

According to an aspect of the present invention, a fibroblast growth factor family production promoter or a fibroblast growth factor family production promoter raw material containing a supernatant of a culture medium used during a reprogramming of somatic cells is provided.

According to an aspect of the present invention, a vascular endothelial cell growth factor production promoter or a vascular endothelial cell growth factor production promoter raw material containing a supernatant of a culture medium used during a reprogramming of somatic cells is provided.

According to an aspect of the present invention, a wound treatment agent or a wound treatment agent raw material containing a supernatant of a culture medium used during a reprogramming of somatic cells is provided.

According to an aspect of the present invention, an epidermal cell growth promoter or an epidermal cell growth promoter raw material containing a supernatant of a culture medium used during a reprogramming of somatic cells is provided.

According to an aspect of the present invention, a pharmaceutical composition or a pharmaceutical composition raw material containing a stem cell extract is provided.

The stem cell extract in the aforementioned pharmaceutical composition or pharmaceutical composition raw material may be a paste, or the stem cell extract may be freeze-dried.

According to an aspect of the present invention, an agent for preventing or ameliorating formation of any of skin blemishes, skin wrinkles, and skin sagging containing the aforementioned pharmaceutical composition or pharmaceutical composition raw material is provided.

According to an aspect of the present invention, a cosmetic composition or a cosmetic composition raw material containing a stem cell extract is provided.

The stem cell extract in the aforementioned cosmetic composition or cosmetic composition raw material may be a paste, or the stem cell extract may be freeze-dried.

According to an aspect of the present invention, an agent for preventing or ameliorating formation of any of skin blemishes, skin wrinkles, and skin sagging containing the aforementioned cosmetic composition or cosmetic composition raw material is provided.

According to an aspect of the present invention, a collagen production promoter or a collagen production promoter raw material containing a stem cell extract is provided.

The stem cell extract in the aforementioned collagen production promoter or collagen production promoter raw material may be a paste, or the stem cell extract may be freeze-dried.

According to an aspect of the present invention, a hair growth agent, hair growth agent raw material, hair restoration agent, or hair restoration agent raw material containing a stem cell extract is provided.

The stem cell paste in the aforementioned hair growth agent, hair growth agent raw material, hair restoration agent, or hair restoration agent raw material may be a paste, or the stem cell extract may be freeze-dried.

According to an aspect of the present invention, a hair papilla cell activator or a hair papilla cell activator raw material containing a stem cell extract is provided.

The stem cell extract in the aforementioned hair papilla cell activator or hair papilla cell activator raw material may be a paste, or the stem cell extract may be freeze-dried.

According to an aspect of the present invention, a fibroblast growth factor family production promoter or a fibroblast growth factor family production promoter raw material containing a stem cell extract is provided.

The stem cell extract in the aforementioned fibroblast growth factor family production promoter or fibroblast growth factor family production promoter raw material may be a paste, or the stem cell extract may be freeze-dried.

According to an aspect of the present invention, a vascular endothelial cell growth factor production promoter or a vascular endothelial cell growth factor production promoter raw material containing a stem cell extract is provided.

The stem cell extract in the aforementioned vascular endothelial cell growth factor production promoter or vascular endothelial cell growth factor production promoter raw material may be a paste, or the stem cell extract may be freeze-dried.

According to an aspect of the present invention, a wound treatment agent or a wound treatment agent raw material containing a stem cell extract is provided.

The stem cell extract in the aforementioned wound treatment agent or wound treatment agent raw material may be a paste, or the stem cell extract may be freeze-dried.

According to an aspect of the present invention, an epidermal cell growth promoter or an epidermal cell growth promoter raw material containing a stem cell extract is provided.

The stem cell extract in the aforementioned epidermal cell growth promoter or epidermal cell growth promoter raw material may be a paste, or the stem cell extract may be freeze-dried.

According to an aspect of the present invention, a method for screening for anti-ultraviolet substances including: providing skin cells by induction of differentiation from pluripotent stem cells produced from somatic cells derived from an aging disease patient or a skin disease patient; irradiating the skin cells with ultraviolet radiation; culturing the UV-irradiated skin cells respectively in a plurality of different solutions; and selecting a culture medium for which a UV-induced damage to the skin cells is little or a solution for which the ultraviolet-dosed skin cells are rapidly recovered, is provided.

According to an aspect of the present invention, a method for screening for anti-dryness substances including: providing skin cells by induction of differentiation from pluripotent stem cells produced from somatic cells derived from an aging disease patient or a skin disease patient; drying the skin cells; culturing the dried skin cells respectively in a plurality of different solutions; and selecting a solution that exhibits a high skin cell survival rate, is provided.

According to an aspect of the present invention, a method for screening for anti-dryness substances including: providing skin cells by induction of differentiation from pluripotent stem cells produced from somatic cells derived from an aging disease patient or a skin disease patient; drying the skin cells; culturing the dried skin cells respectively in a plurality of different solutions; and selecting a solution for which a damage to the tight junctions in the skin cells, is little is provided.

At least one of occludin and claudin in the tight junctions may be analyzed in the aforementioned method.

According to an aspect of the present invention, a method for screening for anti-oxidation stress substances including: providing skin cells by induction of differentiation from pluripotent stem cells produced from somatic cells derived from an aging disease patient or a skin disease patient; subjecting the skin cells to oxidation stress; culturing the oxidatively stressed skin cells respectively in a plurality of different solutions; and selecting a solution that exhibits a high skin cell survival rate, is provided.

According to an aspect of the present invention, a method for screening for moisturizing-promoting substances including: providing skin cells by induction of differentiation from pluripotent stem cells produced from somatic cells derived from an aging disease patient or a skin disease patient; culturing the skin cells respectively in a plurality of different solutions; and selecting, from the plurality of different solutions, a solution that has a large amount of a natural moisturizing factor derived from the skin cells, is provided.

The natural moisturizing factor in the aforementioned method may be at least one of ceramide and filaggrin.

According to an aspect of the present invention, a method for assessing ultraviolet resistance of skin including: providing skin cells by induction of differentiation from pluripotent stem cells produced from somatic cells derived from a subject; and assessing damage to the skin cells due to ultraviolet radiation, is provided.

According to an aspect of the present invention, a method for assessing drying resistance of skin including: providing skin cells by induction of differentiation from pluripotent stem cells produced from somatic cells derived from a subject; drying the skin cells; and assessing a survival rate of the skin cells, is provided.

According to an aspect of the present invention, a method for assessing the drying resistance of skin including: providing skin cells by induction of differentiation from pluripotent stem cells produced from somatic cells derived from a subject; drying the skin cells; and assessing damage to tight junctions in the skin cells, is provided.

At least one of occludin and claudin in the tight junctions may be analyzed in assessment of damage to the tight junctions in the skin cells in the aforementioned method.

According to an aspect of the present invention, a method for assessing the oxidation stress resistance of skin including: providing skin cells by induction of differentiation from pluripotent stem cells produced from somatic cells derived from a subject; subjecting the skin cells to oxidation stress; and assessing a survival rate of the skin cells, is provided.

According to an aspect of the present invention, a method for assessing the moisturizing capacity of skin including: providing skin cells by induction of differentiation from pluripotent stem cells produced from somatic cells derived from a subject; culturing the skin cells; and assessing an amount of a natural moisturizing factor derived from the skin cells, is provided.

Advantageous Effects of Invention

The present invention can provide a pharmaceutical composition and a cosmetic composition that effectively utilize the culture medium from iPS cells.

BRIEF DESCRIPTION OF DRAWINGS

FIG. 7 is a table that gives the results of the VEGF production test in hair papilla cells, according to Example 6.
FIG. 9 is a table that gives the results of the FGF-7 production test in hair papilla cells, according to Example 7.
FIG. 16 is a micrograph of cells according to a reference example.
FIG. 17 is a micrograph of cells according to a reference example.

DESCRIPTION OF EMBODIMENTS

Figure 1:
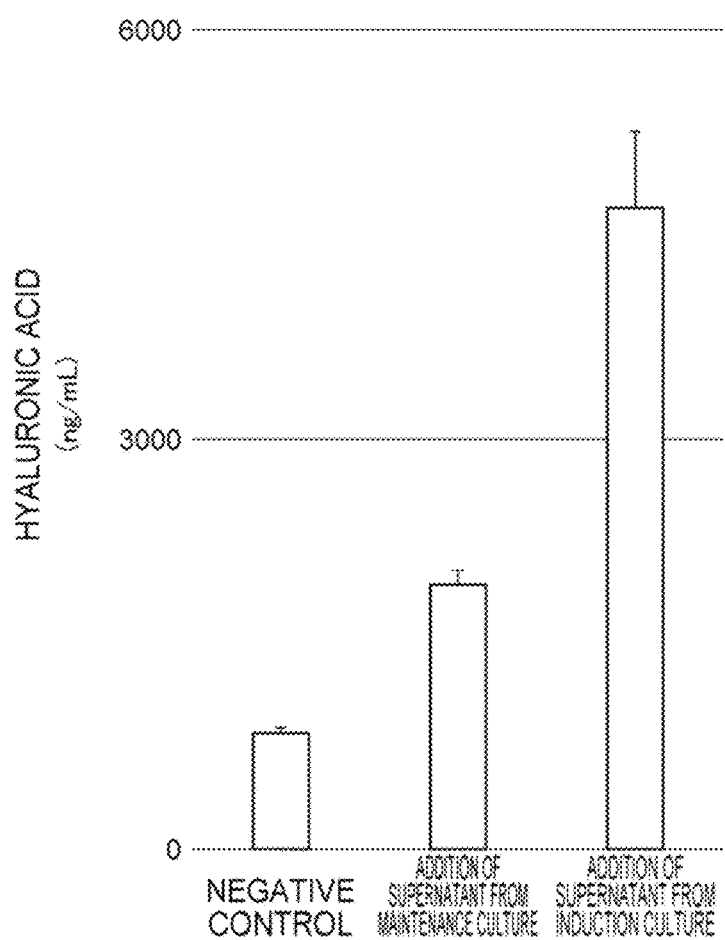
FIG. 1 is a graph that shows the results of a hyaluronic acid production test in fibroblasts, according to Example 2.

Embodiments of the invention are described in detail in the following. The embodiments described below are examples of apparatuses and methods for implementing the technical concept of the invention, and the technical concept of the invention is not limited to the following with regard to, e.g., the combinations of constituent members and so forth. The technical concept of the invention may incorporate various modifications within the scope of the claims.

First Embodiment

The pharmaceutical composition, pharmaceutical composition raw material, cosmetic composition, and cosmetic composition raw material according to a first embodiment each contain a supernatant of a culture medium used during a reprogramming of somatic cells to pluripotent stem cells such as iPS cells and so forth. The pharmaceutical composition, pharmaceutical composition raw material, cosmetic composition, and cosmetic composition raw material according to the first embodiment may each contain a freeze-dried material from the supernatant of a culture medium used during a reprogramming of somatic cells to pluripotent stem cells such as iPS cells and so forth. For each of the pharmaceutical composition, pharmaceutical composition raw material, cosmetic composition, and cosmetic composition raw material according to the first embodiment, the supernatant of a culture medium used during a reprogramming of somatic cells to pluripotent stem cells such as iPS cells and so forth, may be contained in a capsule such as a nanocapsule, or in an emulsion such as a nanoemulsion.

iPS cells are induced, for example, by the introduction of reprogramming factors such as OCT3/4, KLF4, c-MYC, and SOX2, into a somatic cell such as a differentiated cell such as a blood cell or a fibroblast. Induction to iPS cells may be referred to as reprogramming, transformation, transdifferentiation or lineage reprogramming, and cell fate reprogramming. The pluripotent stem cells may be induced during a three-dimensional culture such as suspension culture. A gel culture medium or a liquid culture medium may be used in the case of a three-dimensional culture. Pluripotent stem cells have, for example, a rate of positive of at least 30%, at least 50%, and preferably at least 80% for any of TRA1-60, OCT3/4, SSEA3, SSEA4, TRA1-81, and NANOG. The gel culture medium may not contain feeder cells.

The culture medium used during the induction culture may be, for example, a human ES/IPS culture medium, e.g., TeSR2 (STEMCELL Technologies). The culture medium is not limited to this and various other stem cell culture media can be used. The following, for example, may be used: Primate ES Cell Medium, Reprostem, ReproFF, ReproFF2, and ReproXF (REPROCELL); mTeSR1, TeSRE8, and ReproTeSR (STEMCELL Technologies); PluriSTEM (registered trademark) Human ES/iPS Medium (Merck); NutriStem (registered trademark) XF/FF Culture Medium for Human iPS and ES Cells and Pluriton reprogramming medium (Stemgent); PluriSTEM (registered trademark), StemFit AK02N, and StemFit AK03 (Ajinomoto); ESC-Sure (registered trademark) serum and feeder free medium for hESC/iPS (Applied StemCell); L7 (registered trademark) hPSC Culture System (LONZA); and Primate ES Cell Medium (REPROCELL).

The gel culture medium is prepared, for example, by the addition to a culture medium as indicated above of a deacylated gellan gum so as to provide a final concentration thereof of from 0.001 wt % to 0.5 wt %, from 0.005 wt % to 0.1 wt %, or from 0.01 wt % to 0.05 wt %.

The gel culture medium may contain one or more polymer compounds selected from the group consisting of gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts of the preceding. The gel culture medium may also contain methyl cellulose. The methyl cellulose contained in the medium provides a greater inhibition of aggregation between the cells.

Alternatively, the gel culture medium may contain at least one temperature-sensitive gel selected from poly(glycerol monomethacrylate) (PGMA); poly(2-hydroxypropyl methacrylate) (PHPMA); poly(N-isopropylacrylamide) (PNIPAM); amine-terminated, carboxylic acid-terminated, maleimide-terminated N-hydroxysuccinimide (NHS); ester-terminated, triethoxysilane-terminated poly(N-isopropylacrylamide-co-acrylamide); poly(N-isopropylacrylamide-co-acrylic acid); poly(N-isopropylacrylamide-co-butyl acrylate); poly(N-isopropylacrylamide-co-methacrylic acid); poly(N-isopropylacrylamide-co-methacrylic acid-co-octadecyl acrylate); and N-isopropylacrylamide.

Alternatively, the pharmaceutical composition, pharmaceutical composition raw material, cosmetic composition, and cosmetic composition raw material according to the first embodiment each contain an extract from stem cells. The extract may be a liquid. That is, the extract may be a extract liquid. The stem cells include pluripotent stem cells such as iPS cells, as well as embryonic stem cells (ES cells). The stem cells have, for example, a rate of positive of at least 30%, at least 50%, and preferably at least 80% for TRA1-60 or Oct3/4. In the case of the maintenance culture of the stem cells in an undifferentiated state, the culture medium contains at least 10 ng/mL and preferably at least 40 ng/ml of b-FGF. For each of the pharmaceutical composition, pharmaceutical composition raw material, cosmetic composition, and cosmetic composition raw material, the stem cell extract may be a paste of the stem cells. The paste of the stem cells is obtained by grinding the iPS cells. The stem cell extract may be a freeze-dried material. The stem cell extract may also be a powder. In the alternative, the stem cell extract may be a lysate of the stem cells.

The pharmaceutical composition according to the first embodiment may be a skin liniment composition. The pharmaceutical composition according to the first embodiment may be a skin disease treatment agent. Diseases that can be treated with the skin disease treatment agent according to the first embodiment can be exemplified by acne vulgaris, psoriasis vulgaris, keloid, seborrheic dermatitis, contact dermatitis, atopic dermatitis, atopic xeroderma, dermatoporosis, solar elastosis, actinic keratosis, blepharoptosis, alopecia areata, alopecia, eyelash hypotrichosis, liver spots, age-related pigmentation, heat rash, freckles, delayed-onset bilateral Ota's nevus, seborrheic keratosis, accelerated aging disease-related skin diseases, and herpes simplex.

Conditions that can be ameliorated or eliminated by the cosmetic composition according to the first embodiment can be exemplified by blemishes, freckles, wrinkles, sagging, coarse skin, reduced skin tightness, lack of luster, sensitive skin, dry skin, and thin hair. The effects of the cosmetic composition according to the first embodiment can be exemplified by skin toning, skin texture improvement, maintenance of skin health, prevention of skin roughening, skin tightening, skin moisturizing, replenishment and maintenance of skin moisture and oils, maintenance of skin softness, skin protection, prevention of skin dryness, skin softening, providing skin elasticity, providing skin luster, skin smoothing, providing skin elasticity, reducing the visibility of blemishes, minimizing wrinkles, and skin whitening. In addition, effects of the cosmetic composition according to the first embodiment in relation to the scalp and hair include maintenance of a healthy scalp, hair restoration, prevention of hair thinning, prevention of itching, prevention of alopecia, promoting hair generation, promoting hair growth, preventing post-disease and postpartum alopecia, and hair nourishment.

The pharmaceutical composition according to the first embodiment may be a wound treatment agent, an epidermal cell growth promoter, an epidermal turnover promoter, a hair growth agent, a hair restoration agent, or an eyelash hypotrichosis treatment agent. The pharmaceutical composition and cosmetic composition according to the first embodiment may be a collagen production promoter, a hyaluronic acid production promoter, a hair growth agent, a fibroblast growth factor (FGF) family production promoter, or a vascular endothelial cell growth factor (VEGF) production promoter.

Hair matrix cells at the hair root divide during hair growth, and the cells produced from this make up the hair. Hair growth takes place in a cycle known as the hair cycle, in which an anagen phase, catagen phase, and telogen phase are repeated. Hair papilla cells exercise an effect on the proliferation and differentiation of hair follicle epithelial stem cells through the production and release of growth factors, thus controlling the hair cycle. It is considered that the activation of hair papilla cells and hair matrix cells contributes to the mechanism of hair growth. In addition, active remodeling of blood vessels takes place in the hair follicle in correspondence to the hair cycle, but when angiogenesis is impaired during this cycle, the supply of nutrients and oxygen becomes insufficient for hair formation. It is considered that deficient blood flow from the hair follicle vascular network contributes to the pathology of androgenetic alopecia (AGA).

The following is known with regard to hair papilla cell genes and hair generation and growth. That is, FGF-7 and IGF-1, inter alia, are known as growth factors secreted by papilla cells for hair matrix cells. These factors function to maintain hair follicle growth. Vascular endothelial growth factor (VEGF) is secreted by hair papilla cells and is involved in the growth of hair follicle blood vessels, and also has an autocrinic effect of causing hair papilla cell proliferation; however, its expression level declines moving from the anagen phase to the catagen phase. VEGF gene expression is reduced in the hair tissue of AGA (androgenetic alopecia). VEGFB binds competitively to VEGFR-1, which is the receptor on which VEGF acts. VEGFB exhibits activity that enhances the proliferation and permeability of vascular endothelial cells, but its effect in hair follicles is unclear.

By acting directly on the hair papilla to promote hair growth by increasing the production of FGF-7 that is a hair growth promotion factor, the pharmaceutical composition and cosmetic composition according to the first embodiment have the effect of lengthening the anagen phase of the hair cycle and growing strong, thick hair from thin, weak hair. The pharmaceutical composition and cosmetic composition according to the first embodiment also have the effect of increasing vascular endothelial growth factor (VEGF), which is secreted by hair papilla cells, and, in connection with the proliferation of hair follicle blood vessels, also autocrinically causing proliferation of hair papilla cells. Accordingly, the pharmaceutical composition and cosmetic composition according to the first embodiment can be used as activators of hair papilla cells.

In the case where the pharmaceutical composition and cosmetic composition according to the first embodiment are used as a hair restoration agent or hair growth agent, the compositions may contain other active ingredients such as minoxidil, swertia, pantothenyl ethyl ether, tocopherol acetate, dipotassium glycyrrhizinate, adenosine, and so forth.

Wounds treatable by the wound treatment agent according to the first embodiment can be exemplified by burns, abrasions, lacerations, bruises, suture wounds, bedsores, and skin defect wounds.

The pharmaceutical composition and cosmetic composition according to the first embodiment contain an effective amount of the supernatant of the culture medium used during the reprogramming of somatic cells. In the alternative, the pharmaceutical composition and cosmetic composition according to the first embodiment contain an effective amount of the extract of stem cells. The effective amount referred to here is an amount capable of exhibiting an effect as a pharmaceutical composition or cosmetic composition. The effective amount is established as appropriate according to the age of the patient, the targeted disease, the presence/absence of other effective ingredients, and the amounts of other admixtures.

The pharmaceutical composition and cosmetic composition according to the first embodiment may also contain formulation-acceptable carriers, excipients, disintegrants, buffering agents, emulsifiers, suspending agents, sedatives, stabilizers, preservatives, antiseptics, physiological saline, and so forth. The excipients can be exemplified by lactose, starch, sorbitol, D-mannitol, and sucrose. The disintegrants can be exemplified by carboxymethyl cellulose and calcium carbonate. The buffering agents can be exemplified by phosphates, citrates, and acetates. The emulsifiers can be exemplified by gum arabic, sodium alginate, and tragacanth.

The suspending agents can be exemplified by glycerol monostearate, aluminum monostearate, methyl cellulose, carboxymethyl cellulose, hydroxymethyl cellulose, and sodium lauryl sulfate. The sedatives can be exemplified by benzyl alcohol, chlorobutanol, and sorbitol. The stabilizers can be exemplified by propylene glycol and ascorbic acid. The preservatives can be exemplified by phenol, benzalkonium chloride, benzyl alcohol, chlorobutanol, and methylparaben. The antiseptics can be exemplified by benzalkonium chloride, para-oxybenzoic acid, and chlorobutanol.

The pharmaceutical composition and cosmetic composition according to the first embodiment may additionally contain the following within a range in which the objectives for the pharmaceutical composition and cosmetic composition according to the first embodiment are achieved: water, an alcohol, a surfactant (cationic, anionic, nonionic, or amphoteric surfactant), a humectant (e.g., glycerol, 1,3-butylene glycol, propylene glycol, propanediol, pentanediol, polyquaternium, an amino acid, urea, a pyrrolidonecarboxylate salt, a nucleic acid, a monosaccharide, an oligosaccharide, and derivatives of the preceding), a thickener (e.g., a polysaccharide, polyacrylate salt, carboxyvinyl polymer, polyvinylpyrrolidone, polyvinyl alcohol, chitin, chitosan, alginic acid, carrageenan, xanthan gum, methyl cellulose, and derivatives of the preceding), a wax, vaseline, a hydrocarbon saturated fatty acid, an unsaturated fatty acid, a silicone oil, a derivative of the preceding, a triglyceride such as glyceryl tri(caprylate/caprate) or glyceryl trioctanoate, an ester oil such as isopropyl stearate, a natural fat or oil (e.g., olive oil, camellia oil, avocado oil, almond oil, cocoa butter, evening primrose oil, grape seed oil, macadamia nut oil, eucalyptus oil, rosehip oil, squalane, orange roughy oil, lanolin, and ceramide), an antiseptic agent (e.g., oxybenzoic acid derivatives, dehydroacetate salts, photosensitizer, sorbic acid, phenoxyethanol, and derivatives of the preceding), a microbicide (e.g., sulfur, triclocarbanilide, salicylic acid, zinc pyrithione, hinokitiol, and derivatives of the preceding), an ultraviolet absorber (e.g., para-aminobenzoic acid, methoxycinnamic acid, and derivatives of the preceding), an anti-inflammatory agent (e.g., allantoin, bisabolol, ε-aminocaproic acid, acetyl farnesylcysteine, glycyrrhizinic acid, and derivatives of the preceding), an antioxidant (e.g., tocopherol, BHA, BHT, astaxanthin, and derivatives of the preceding), a chelating agent (e.g., edetic acid, hydroxyethanediphosphonic acid, and derivatives of the preceding), an animal or plant extract (e.g., ashitaba, aloe, rose fruit, scutellaria root, phellodendron bark, sea weed, Chinese quince, camomile, licorice, kiwi, cucumber, mulberry, white birch, *Angelica acutiloba*, garlic, peony, hop, horse chestnut, lavender, rosemary, eucalyptus, milk, various peptides, placenta, royal jelly, Euglena extract, hydrolyzed Euglena extract, Euglena oil, and purified products and fermentation products containing their components), a pH regulator (e.g., an inorganic acid, inorganic acid salt, organic acid, organic acid salt, and derivatives of the preceding), a vitamin (e.g., vitamin A group, vitamin B group, vitamin C, vitamin D group, ubiquinone, nicotinamide, and derivatives of the preceding), a fermented liquid from yeast, *Aspergillus*, or lactic acid bacteria, a *Galactomyces* culture solution, a skin whitener (e.g., tranexamic acid, cetyl tranexamate hydrochloride, 4-n-butylresorcinol, arbutin, kojic acid, ellagic acid, licorice flavonoid, niacinamide, and vitamin C derivatives), a ceramide or ceramide derivative, an anti-wrinkle agent (e.g., retinol and retinal and their derivatives, nicotinamide, an oligopeptide, derivatives of the preceding, a neutrophil elastase inhibitor, and natural and synthetic components with an inhibiting effect on MMP-1 and MMP-2), and titanium oxide, talc, mica, silica, zinc oxide, iron oxide, silicon, and their processed powders.

Components that may be added to the pharmaceutical composition and cosmetic composition according to the first embodiment are not limited to those indicated above, and any components usable in pharmaceutical compositions and cosmetic compositions may be selected. In the case where the pharmaceutical composition or cosmetic composition according to the first embodiment is to be used as a poultice, a base (e.g., kaolin, bentonite) or a gelling agent (e.g., polyacrylate salt, polyvinyl alcohol) may be incorporated-in addition to the aforementioned components-in a range that achieves the objectives. In the case where the pharmaceutical composition or cosmetic composition according to the first embodiment is to be used as a bath additive, a sulfate salt, bicarbonate salt, borate salt, colorant, and humectant may be added as appropriate within a range that achieves the objectives, and the composition may be prepared as a powder or liquid.

The pharmaceutical composition and cosmetic composition according to the first embodiment can be manufactured using methods commonly known in the pertinent technical field.

Second Embodiment

The method for screening for anti-ultraviolet substances according to a second embodiment includes: providing skin cells by the induction of differentiation from iPS cells produced from somatic cells derived from an aging disease patient or a skin disease patient such as an accelerated aging disease patient, skin disease patient, and so forth; optionally irradiating the skin cells, for which differentiation has been induced, with ultraviolet radiation; culturing the UV-irradiated skin cells in each of a plurality of different solutions;

and selecting a solution for which a UV-induced damage to the skin cells is little or a solution for which the ultraviolet-dosed skin cells are rapidly recovered. The patient is not limited to humans, and non-human animals are also included.

The accelerated aging disease can be exemplified by Werner syndrome, xeroderma pigmentosum, and Cockayne syndrome, but is not limited to these. The somatic cells from the accelerated aging disease patient can be exemplified by fibroblasts, blood cells, epithelial cells, somatic stem cells, keratinocytes, hair papilla cells, and dental pulp stem cells, but are not limited to these. The iPS cells are induced by the introduction of reprogramming factors such as OCT3/4, KLF4, c-MYC, SOX2, and so forth, into the somatic cells from the accelerated aging disease patient. For the induction of differentiation of skin cells from the iPS cells, for example, the iPS cells are seeded to, for example, a low-cell-attachment dish containing a culture solution that does not contain bFGF. Thereafter, culture medium is exchanged every two days. The embryoid bodies (EB) formed after eight days are seeded to a dish and the cells are attached to the dish. The cells are cultured in 10% FBS culture medium. When the cells have become confluent, the cells are detached from the dish using trypsin and are passaged. Passage is similarly repeated for one month. Thereafter, using a fibroblast marker such as CD13, it is confirmed that the cells have differentiated into fibroblasts. Confirmation that undifferentiated iPS cells do not remain in the cells may also be carried out using an iPS cell marker such as TRA-1-60. The differentiation-induced skin cells are, for example, skin fibroblasts, but are not limited to these.

The differentiation-induced skin cells are cultured as appropriate and are then exposed to ultraviolet radiation (UV). The intensity of the ultraviolet radiation, the wavelength range, and the exposure time are established as appropriate in conformity with, e.g., the application, method of use, and use amount of the anti-ultraviolet substance for which screening is being carried out. The UV-irradiated skin cells are cultured in each of a plurality of different solutions that each contain a different substance to be screened. The solution may be a culture medium. The screening target substance in the solution, the culture time, and so forth are established as appropriate in conformity with, for example, the application, method of use, and use amount of the anti-ultraviolet substance to be screened.

Thereafter, a solution for which skin cell damage is little, or a solution for which skin cell recover is rapid, is selected as a solution that contains an anti-ultraviolet substance. For example, the skin cells cultured in each of the plurality of solutions are analyzed, and a solution or group of solutions used in the culture of low-damage skin cells is selected and a solution or group of solutions used in the culture of high-damage skin cells is rejected. Alternatively, the skin cells cultured in each of the plurality of solutions are analyzed, and a solution or group of solutions used in the culture of rapidly recovered skin cells is selected and a solution or group of solutions used in the culture of slowly recovered skin cells or unrecovered skin cells is rejected.

According to findings by the present inventors, skin cells induced from iPS cells that have been induced from somatic cells derived from aging disease patients or skin disease patients such as accelerated aging disease patients, skin disease patients, and so forth, tend to lack an ability to resist UV irradiation as compared to the skin cells of healthy individuals. Screening can therefore be carried out for effective anti-ultraviolet substances by using skin cells induced from iPS cells that have been induced from somatic cells derived from aging disease patients or skin disease patients such as accelerated aging disease patients, skin disease patients, and so forth.

Third Embodiment

The method for assessing the ultraviolet resistance of skin according to a third embodiment includes: providing skin cells by the induction of differentiation from pluripotent stem cells produced from somatic cells derived from a subject; irradiating the skin cells with ultraviolet radiation; and assessing damage to the skin cells due to the ultraviolet radiation.

The subject may be a disease patient or may be a healthy individual. The somatic cells derived from a subject may be acquired from the subject in advance, and the method may thus not include a step of acquiring somatic cells from a subject. In the case where the ultraviolet-induced damage to the skin cells is large, the skin cells of the subject may then be assessed as not having ultraviolet resistance. In the case where ultraviolet-induced damage to the skin cells is little, the skin cells of the subject may then be assessed as having ultraviolet resistance. An assessment of whether the skin cells of a subject exhibit ultraviolet resistance can thus be made based on the results of the assessment of ultraviolet-induced damage to the skin cells according to the method.

Fourth Embodiment

The method for screening for anti-dryness substances according to a fourth embodiment includes: providing skin cells by the induction of differentiation from iPS cells produced from somatic cells derived from an aging disease patient or skin disease patient such as an accelerated aging disease patient, skin disease patient, and so forth; drying the skin cells; culturing the dried skin cells in each of a plurality of different solutions; and selecting a solution that exhibits a high skin cell survival rate.

The skin cells, for which differentiation has been induced as in the second embodiment, are cultured as appropriate and are then dried. During the drying of the skin cells, for example, the culture medium surrounding the skin cells is removed. An air current may be directed onto the skin cells or the skin cells may be dried using, for example, a drying agent. The method for drying skin cell and drying time are established as appropriate in conformity with, e.g., the application, method of use, and use amount of the anti-dryness substance to be screened. The dried skin cells are cultured in each of a plurality of different solutions that each contain a different substance to be screened. The solution may be a culture medium. The screening target substance in the solution, the culture time, and so forth are established as appropriate in conformity with, for example, the application, method of use, and use amount of the anti-dryness substance to be screened.

Thereafter, the survival rate of the skin cells cultured in each of the plurality of solutions is measured, and a solution that exhibits a high skin cell survival rate is selected as a solution that contains an anti-dryness substance. For example, the survival rate of the skin cells cultured in each of the plurality of solutions is measured, and a solution or group of solutions used in the culture of skin cells at a high survival rate is selected and a solution or group of solutions used in the culture of skin cells at a low survival rate is rejected.

A solution associated with little damage to the tight junctions in the skin cells may be selected in place of selection of a solution that provides a high skin cell survival rate. In this case, at least one of occludin and claudin in the tight junctions may be analyzed and a solution may be selected for which the amount of at least one of occludin and claudin is large. When skin cells are dried, generally the tight junctions are damaged and the amounts of occludin and claudin decline. Accordingly, for example, the tight junctions are analyzed for skin cells cultured in each of a plurality of solutions and a solution or group of solutions used in the culture of skin cells with little damage of tight junction is selected, and a solution or group of solutions used in the culture of skin cells with large damage of tight junction is rejected.

According to findings by the present inventors, skin cells induced from iPS cells that have been induced from somatic cells derived from aging disease patients or skin disease patients such as accelerated aging disease patients, skin disease patients, and so forth, tend to lack an ability to resist drying as compared to the skin cells of healthy individuals. Screening can therefore be carried out for effective anti-dryness substances by using skin cells induced from iPS cells that have been induced from somatic cells derived from aging disease patients or skin disease patients such as accelerated aging disease patients, skin disease patients, and so forth.

Fifth Embodiment

The method for assessing the drying resistance of skin according to a fifth embodiment includes: providing skin cells by the induction of differentiation from pluripotent stem cells produced from somatic cells derived from a subject; drying the skin cells; and assessing the survival rate of these skin cells.

The subject may be a disease patient or may be a healthy individual. The somatic cells derived from a subject may be acquired from the subject in advance, and the method may thus not include a step of acquiring somatic cells from a subject. In the case where the skin cell survival rate is high, the skin cells of the subject may then be assessed as having drying resistance. In the case where the skin cell survival rate is low, the skin cells of the subject may then be assessed as lacking drying resistance. An assessment of whether the skin cells of a subject exhibit drying resistance can thus be made based on the results of the assessment of the skin cell survival rate according to the method.

Damage to the tight junctions of the skin cells may be assessed in place of assessment of the skin cell survival rate. In the case where damage of tight junction damage is little, the skin cells of the subject may then be assessed as having drying resistance. In the case where damage of tight junction is large, the skin cells of the subject may then be assessed as lacking drying resistance.

Sixth Embodiment

The method for screening for anti-oxidation stress substances according to a sixth embodiment includes: providing skin cells by the induction of differentiation from iPS cells produced from somatic cells derived from an aging disease patient or a skin disease patient such as an accelerated aging disease patient, skin disease patient, and so forth; subjecting the skin cells to oxidation stress; culturing the oxidatively stressed skin cells in each of a plurality of different solutions; and selecting a solution that exhibits a high skin cell survival rate.

The skin cells, for which differentiation has been induced as in the second embodiment, are cultured as appropriate and are then subjected to oxidation stress. The method for oxidatively stressing the skin cells is not particularly limited, but includes, for example, the addition of an oxidizing substance such as hydrogen peroxide, to the culture medium in which the skin cells are being cultured. The method for applying oxidation stress to the skin cells and the time for applying the oxidation stress to the skin cells are established as appropriate in conformity with, e.g., the application, method of use, and use amount of the anti-oxidation stress substance to be screened. For example, the substance that applies the oxidation stress is removed from the oxidatively stressed cells, which are then cultured in each of a plurality of different solutions that each contain a different substance to be screened. The solution may be a culture medium. The screening target substance in the solution, the culture time, and so forth are established as appropriate in conformity with, for example, the application, method of use, and use amount of the anti-oxidation stress substance to be screened.

Thereafter, the survival rate of the skin cells cultured in each of the plurality of solutions is measured, and a solution that exhibits a high skin cell survival rate is selected as a solution that contains an anti-oxidation stress substance. For example, the survival rate of the skin cells cultured in each of the plurality of solutions is measured, and a solution or group of solutions used in the culture of skin cells at a high survival rate is selected and a solution or group of solutions used in the culture of skin cells at a low survival rate is rejected.

According to findings by the present inventors, skin cells induced from iPS cells that have been induced from somatic cells derived from aging disease patients or skin disease patients such as accelerated aging disease patients, skin disease patients, and so forth, tend to lack an ability to resist oxidation stress as compared to the skin cells of healthy individuals. Screening can therefore be carried out for effective anti-oxidation stress substances by using skin cells induced from iPS cells that have been induced from somatic cells derived from aging disease patients or skin disease patients such as accelerated aging disease patients, skin disease patients, and so forth.

Seventh Embodiment

The method for assessing the oxidation stress resistance of skin according to a seventh embodiment includes: providing skin cells by the induction of differentiation from pluripotent stem cells produced from somatic cells derived from a subject; subjecting the skin cells to oxidation stress; and assessing the survival rate of these skin cells.

The subject may be a disease patient or may be a healthy individual. The somatic cells derived from a subject may be acquired from the subject in advance, and the method may thus not include a step of acquiring somatic cells from a subject. In the case where the oxidation stress-induced damage to the skin cells is large, the skin cells of the subject may then be assessed as lacking resistance to oxidation stress. In the case where oxidation stress-induced damage to the skin cells is little, the skin cells of the subject may then be assessed as having resistance to oxidation stress. An assessment of whether the skin cells of a subject exhibit resistance to oxidation stress can thus be made based on the results of the assessment according to the method of the oxidation stress-induced damage to the skin cells.

Eighth Embodiment

The method according to an eighth embodiment for screening for moisturizing-promoting substances includes:

providing skin cells by the induction of differentiation from pluripotent stem cells produced from somatic cells derived from an aging disease patient or a skin disease patient such as an accelerated aging disease patient, skin disease patient, and so forth; culturing the skin cells in each of a plurality of different solutions; and selecting, from the plurality of different solutions, a solution that has a large amount of a natural moisturizing factor derived from the skin cells.

The skin cells, for which differentiation has been induced as in the second embodiment, are cultured in each of a plurality of different solutions that each contain a different substance to be screened. The screening target substance in the solution, the culture time, and so forth are established as appropriate in conformity with, for example, the application, method of use, and use amount of the moisturizing-promoting substance to be screened.

Thereafter, the amount of a skin cell-derived natural moisturizing factor in each of the plurality of solutions is measured. The natural moisturizing factor is not particularly limited, but can be exemplified by ceramide and filaggrin. A solution having a large amount of a natural moisturizing factor is selected as a solution that contains a moisturizing-promoting substance. For example, the amount of a natural moisturizing factor is measured in each of the plurality of solutions, and a solution or group of solutions containing a large amount of a natural moisturizing factor is selected and a solution or group of solutions containing a small amount of natural moisturizing factor is rejected.

According to findings by the present inventors, as aging or a skin disease progresses, the amount of expression of moisturizing-promoting substances assumes a declining trend for skin cells. Screening can therefore be carried out for effective moisturizing-promoting substances by using skin cells induced from iPS cells that have been induced from somatic cells derived from aging disease patients or skin disease patients such as accelerated aging disease patients, skin disease patients, and so forth.

Ninth Embodiment

The method for assessing the moisturizing capacity of skin according to a ninth embodiment includes: providing skin cells by the induction of differentiation from pluripotent stem cells produced from somatic cells derived from a subject; culturing the skin cells; and assessing the amount of a natural moisturizing factor derived from the skin cells.

The subject may be a disease patient or may be a healthy individual. The somatic cells derived from a subject may be acquired from the subject in advance, and the method may thus not include a step of acquiring somatic cells from a subject. In the case where the amount of a skin cell-derived natural moisturizing factor is large, the skin cells of the subject may be assessed as having a high moisturizing capacity. In the case where the amount of skin cell-derived natural moisturizing factor is little, the skin cells of the subject may be assessed as having a low moisturizing capacity. The method makes it possible to assess whether the skin cells of a subject have a moisturizing capacity based on the results of the assessment of the amount of skin cell-derived natural moisturizing factor.

EXAMPLES

Example 1: Preparation of Culture Medium Used During Culture While Reprogramming Blood Cells to iPS Cells A hematopoietic cell culture medium was prepared by adding growth factor into a serum-free, animal component-free hematopoietic cell culture medium (Stemspan ACF, STEMCELL Technologies). $2 \times 10^5$ blood cells (peripheral blood mononuclear cells) were seeded to each well of a 12-well dish, and the hematopoietic cell gel culture medium was dripped into each well to suspend the blood cells in the hematopoietic cell gel culture medium. The 12-well dish was then stand still in a $CO_2$ incubator at 37° C. and the cells were suspension cultured.

After 3 days after the cell culture was initiated, the hematopoietic cell gel culture medium was appropriately added to each well. After 6 days after the start of cell culture, gene was introduced into the cells by the addition to the culture medium in each well of a Sendai virus vector kit for iPS cell production (CytoTune 2.0 Reprogramming Kit, registered trademark, ThermoFisher) such that the virus titer was from 1 to 20, or gene was introduced into the cells by electroporation of an episomal plasmid (ThermoFisher). Thereafter, gel culture medium was added to each well and the cells were cultured.

A stem cell gel culture medium was prepared by adding gellan gum to an hES culture medium to a final concentration of 0.02%. Beginning 2 days after infection, 2 mL of the stem cell gel culture medium was added to each well once every 2 days. At 14 days post-infection, the induction of iPS cell masses was confirmed, and the gel culture medium supernatant was recovered. The recovered gel culture medium supernatant was sterilized by filtration with a filter, and the gel culture medium supernatant that passed through the filter was designated as the reprogramming culture medium supernatant according to Example 1.

Reference Example 1: Preparation of Culture Medium used During Culture while Maintaining iPS Cells in the Undifferentiated State Using mTeSR1 (registered trademark, STEMCELL Technologies) or StemFit (registered trademark, Ajinomoto), human iPS cells were adhesion maintenance cultured on an adhesion culture dish coated with Matrigel (registered trademark, Corning) or Laminin 511. The human iPS cells were passaged each week. Treatment with an ES cell dissociation solution (TrypLE Select, registered trademark, ThermoFisher) was carried out at passage.

Using an ES cell dissociation solution (TrypLE Select, registered trademark, ThermoFisher), the human iPS cells that had been maintenance cultured as described above were detached from the adhesion culture dish and divided into single cells. Gellan gum and 10 µmol/L ROCK inhibitor (Selleck) were then added; the human iPS cells were seeded to the gelled stem cell culture medium; and the human iPS cells were suspension cultured for 14 days. During the 14-day suspension culture, the incubation vessel was replenished with the gelled stem cell culture medium once every 2 days.

The gelled stem cell culture medium in which the human iPS cells were suspended was then filtered with a mesh filter to remove the cell masses. The filtered gelled stem cell culture medium was centrifuged for 5 minutes at 1500 g to sediment the cells and gel; after centrifugation, the stem cell culture medium supernatant was recovered again and then centrifuged for 3 minutes at 3,000 rpm; and after centrifugation the stem cell culture medium supernatant was filtered on a 0.22 µm filter. The stem cell culture medium supernatant provided by filtration was designated as the supernatant according to Reference Example 1 of culture medium used for the maintenance culture of iPS cells.

The maintenance-cultured iPS cells were confirmed to be positive for the undifferentiation markers NANOG, OCT3/4, and TRA-1-60.

Example 2: Test of Hyaluronic Acid Production by Fibroblasts

DMEM culture medium supplemented with 10% FBS and 1% penicillin-streptomycin was prepared as growth culture medium A. Adult-derived normal human fibroblasts (KF-4109, Strain No. 01035, Kurabo Industries, Ltd.) were then suspended in growth culture medium A to a concentration of $5 \times 10^3$ cells/0.1 mL/well and were seeded to 96-well plates and were cultured for 1 day in a $CO_2$ incubator (5% $CO_2$, 37° C.).

DMEM culture medium supplemented with 10% FBS and 1% penicillin-streptomycin was prepared as test culture medium A. The test culture medium A was mixed with the supernatant solutions according to Example 1 and Reference Example 1, respectively to obtain a culture medium A supplemented with the supernatant according to Example 1 at a concentration of 10% and a culture medium A supplemented with the supernatant according to Reference Example 1 at a concentration of 10%. The growth culture medium A in some of the wells in which the fibroblasts were being cultured was exchanged to, respectively, the culture medium A supplemented with supernatant according to Example 1 or the culture medium A supplemented with supernatant according to Reference Example 1. As a negative control, the growth culture medium A in some of the wells was exchanged to DMEM culture medium that had not been supplemented with FBS, penicillin-streptomycin, and supernatant (non-supplemented test culture medium A).

After the culture medium exchange, the fibroblasts were cultured for 3 days; the supernatant of the culture medium was recovered; and the hyaluronic acid concentration in the culture medium supernatant was measured using DueSet Hyaluronan (Cat. No. DY3614, R & D Systems). The results are shown in FIG. 1. It was revealed that hyaluronic acid production by fibroblasts cultured on the culture medium supplemented with the reprogramming culture medium supernatant according to Example 1 was at least twice that by fibroblasts cultured on the culture medium supplemented with the supernatant according to Reference Example 1 of culture medium used for the maintenance culture of iPS cells.

Example 3: Preparation of iPS Cell Extract Liquid

Using each of Teser1, Teser2, StemFit, Essential8, Teser-E8, and NutriStem, iPS cells were cultured on each of a Matrigel coating and a laminin coating. At the stage at which the iPS cells had reached 80% confluence, the iPS cells were detached from the culture vessel using TrypLE Select, and the solution containing the detached iPS cells was centrifuged for 5 minutes at 200 g and the iPS cells were collected in a 1.5 mL tube. The iPS cell masses were then ground using a pestle (Pestle in G-Tube, ThermoFisher), and the extract liquid of the iPS cells containing a paste of the ground iPS cells was flash frozen using liquid nitrogen. When the iPS cell extract liquid was to be used, the iPS cell extract liquid was suspended in 5 mL of culture medium followed by incubation overnight at 4° C. and centrifugation of the suspension the following day for 10 minutes at 1500 g to remove the ruptured cell fragments from the solution. The solution was then filtered on a filter, and the solution passing through the filter was designated as the iPS cell extract liquid.

Example 4: Test of Production of Type I Collagen by Fibroblasts

The adult-derived normal human fibroblasts were cultured using growth culture medium A in a manner similar to Example 2. The test culture medium A was also prepared in a manner similar to Example 2. The iPS cell extract liquid according to Example 3 was then mixed with test culture medium A to obtain an extract liquid-supplemented culture medium A containing the iPS cell extract liquid according to Example 3 at a concentration of 50.0 v/v % or 100.0 v/v %. The growth culture medium A in some of the wells in which the fibroblasts were being cultured was exchanged to the extract liquid-supplemented culture medium A. As a negative control, the growth culture medium A in some of the wells was exchanged to DMEM culture medium that had not been supplemented with FBS, penicillin-streptomycin, and iPS cell extract liquid (non-supplemented test culture medium A).

Figures 2, 3:
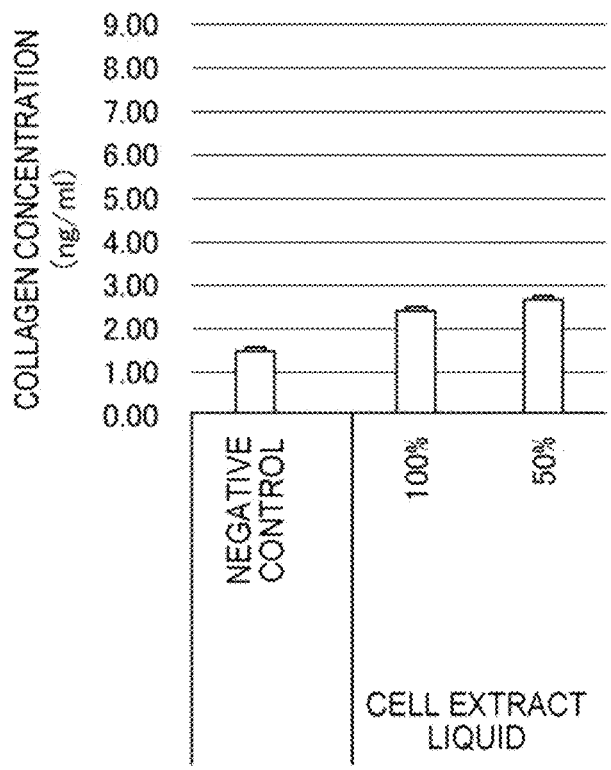
FIG. 2 is a graph that shows the results of a type I collagen production test in fibroblasts, according to Example 4.
FIG. 3 is a table that gives the results of the type I collagen production test in fibroblasts, according to Example 4.

After culture medium exchange, the fibroblasts were cultured for 3 days and the supernatant from the culture medium was recovered and was stored at −80° C. The culture medium supernatant was subsequently thawed and the concentration of type I collagen in the culture medium supernatant was measured using a human collagen type 1 ELISA kit (Cat. No. EC1-E105). The results are shown in FIG. 2 and FIG. 3. The fibroblasts cultured on culture medium supplemented with the iPS cell extract liquid were confirmed to produce more collagen than the fibroblasts cultured on culture medium not supplemented with the iPS cell extract liquid.

Example 5: Hair Papilla Cell Growth Test

A hair papilla cell special culture medium (Cat. No. TMTPGM-250, TOYOBO) supplemented with special-purpose additives (fetal calf serum, insulin/transferrin/triiodothyronine mixture, bovine pituitary extract, cyproterone acetate) was prepared and designated growth culture medium B. Normal human hair papilla cells (Cat. No. CA60205a, Lot. No. 2868, TOYOBO) were then suspended in growth medium B to a concentration of $1.2 \times 10^4$ cells/0.3 mL/well, seeded to a type I collagen-coated 48-well plate, and cultured for 1 day in a $CO_2$ incubator (5% $CO_2$, 37° C.).

The iPS cell extract liquid according to Example 3 was mixed with the non-supplemented hair papilla cell special culture medium (non-supplemented test culture medium B) to obtain an extract liquid-supplemented culture medium B that contained the iPS cell extract liquid according to Example 3 at a concentration of 50.0 v/v % or 100.0 v/v %. As a negative control, the growth culture medium B in some of the wells was exchanged to the hair papilla cell special culture medium to which the additives and iPS cell extract liquid had not been added (non-supplemented test culture medium B).

Figures 4, 5:
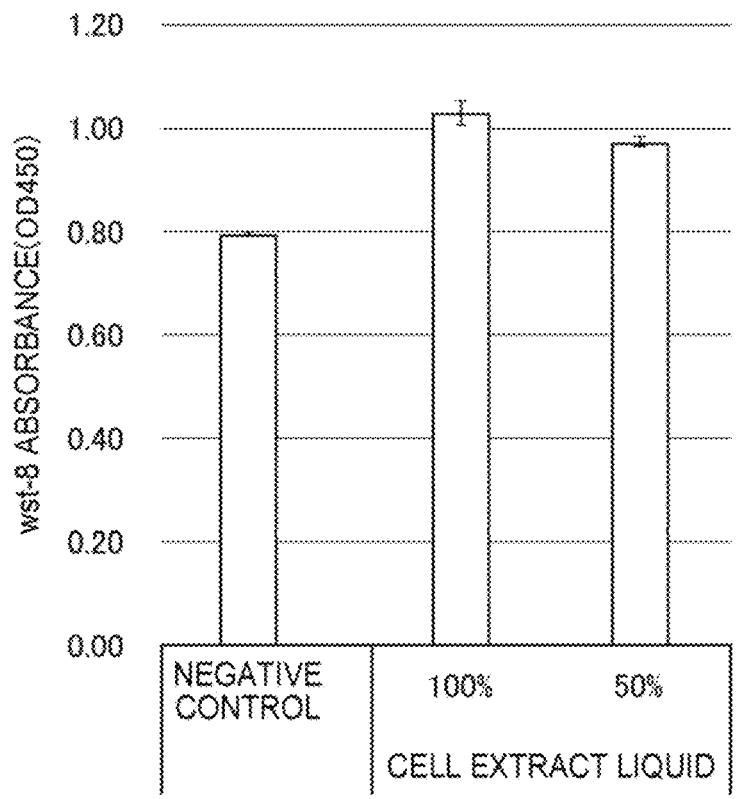
FIG. 4 is a graph that shows the results of the hair papilla cell growth test according to Example 5.
FIG. 5 is a table that gives the results of the hair papilla cell growth test according to Example 5.

The hair papilla cells were cultured for 3 days in the exchanged culture medium, and the viable cells was counted by the WST-8 method. The results are shown in FIG. 4 and FIG. 5. It was confirmed that hair papilla cell growth using the non-supplemented test culture medium B containing the iPS cell extract liquid according to Example 3 was superior to that using the non-supplemented test culture medium B lacking the iPS cell extract liquid. The results therefore suggested that an iPS cell extract liquid has a hair restoration effect and a hair growth effect such as treating thin hair, preventing alopecia, promoting hair formation, and promoting hair growth.

Example 6: Test of VEGF Production by Hair Papilla Cells

Normal human hair papilla cells were cultured for 1 day on growth culture medium B in a manner similar to Example 5. The reprogramming culture medium supernatant according to Example 1 was then added to the growth culture medium B in some of the wells to provide a concentration of 10.0 v/v % or 20.0 v/v %. In addition, the iPS cell extract liquid according to Example 3 was added to the growth culture medium B in some of the wells to provide a concentration of 50.0 v/v % or 100.0 v/v %.

As a negative control, the growth culture medium B in some of the wells was exchanged to non-supplemented test culture medium B. As reference controls, the growth culture medium B in some of the wells was exchanged to an adenosine-supplemented culture medium provided by adding 100 µmol/L adenosine to the hair papilla cell special culture medium, and the growth culture medium B in some of the wells was exchanged to a minoxidil-supplemented culture medium providing by adding 30 µmol/L minoxidil to the hair papilla cell special culture medium. In addition, as a vehicle control for minoxidil, the growth culture medium B in some of the wells was exchanged to a DMSO-supplemented culture medium provided by adding 0.1% DMSO to the hair papilla cell special culture medium.

Figure 6:
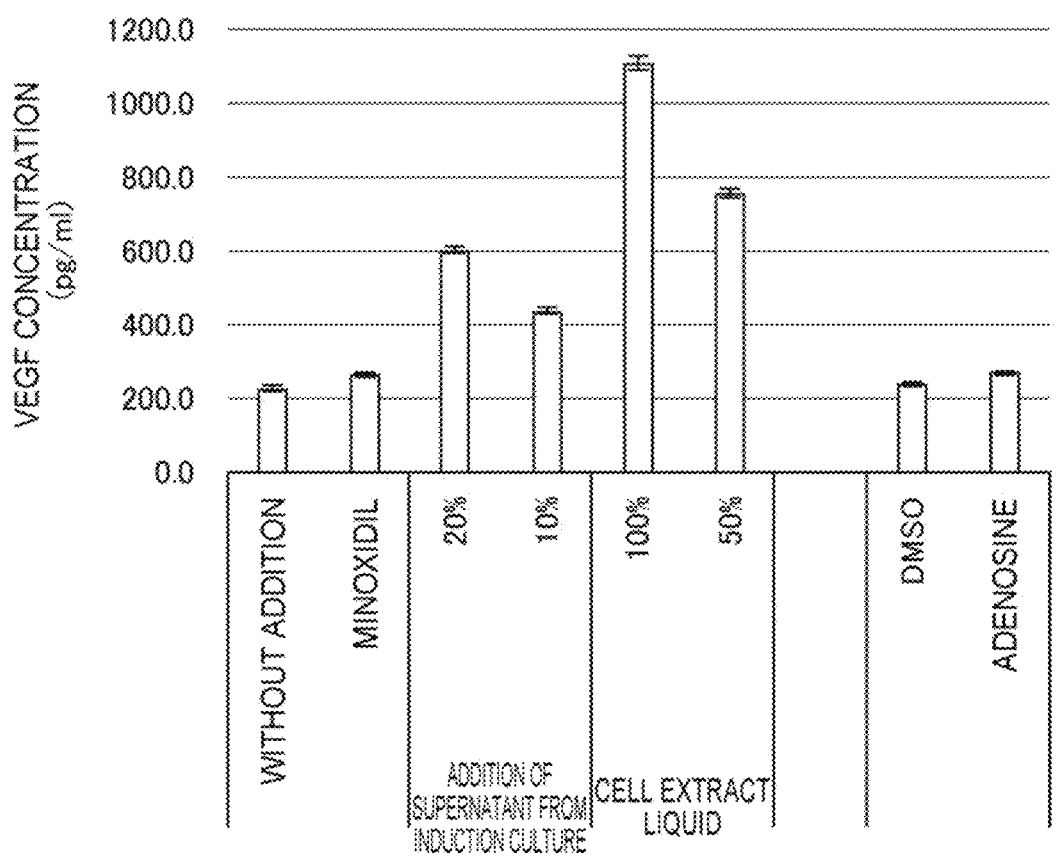
FIG. 6 is a graph that shows the results of a VEGF production test in hair papilla cells, according to Example 6.

After culture medium was exchanged, the hair papilla cells were cultured for 3 days and the culture medium supernatant was recovered and stored at −80° C. The culture medium supernatant was then thawed and the vascular endothelial cell growth factor (VEGF) concentration in the culture medium supernatant was measured using an Human ELISA kit (Cat. No. ab100519, Abcam). The results are shown in FIG. 6 and FIG. 7. It was shown that VEGF production by the hair papilla cells was promoted by the supernatant from culture medium used during iPS cell induction culture and by the iPS cell extract liquid. This suggested that supernatant from a culture medium used during iPS cell induction culture and an iPS cell extract liquid are effective for hair restoration, hair formation, and hair growth.

Example 7: Test of FGF-7 Production by Hair Papilla Cells

Normal human hair papilla cells were cultured for 1 day on growth culture medium B in a manner similar to Example 5. The reprogramming culture medium supernatant according to Example 1 was then added to the growth culture medium B in some of the wells to provide a concentration of 10.0 v/v % or 20.0 v/v %. In addition, the iPS cell extract liquid according to Example 3 was added to the growth culture medium B in some of the wells to provide a concentration of 50.0 v/v % or 100.0 v/v %.

As a negative control, the growth culture medium B in some of the wells was exchanged to non-supplemented test culture medium B. As reference controls, the growth culture medium B in some of the wells was exchanged to an adenosine-supplemented culture medium provided by adding 100 µmol/L adenosine to the hair papilla cell special culture medium, and the growth culture medium B in some of the wells was exchanged to a minoxidil-supplemented culture medium providing by adding 30 µmol/L minoxidil to the hair papilla cell special culture medium. In addition, as a vehicle control for minoxidil, the growth culture medium B in some of the wells was exchanged to a DMSO-supplemented culture medium provided by adding 0.1% DMSO to the hair papilla cell special culture medium.

Figure 8:
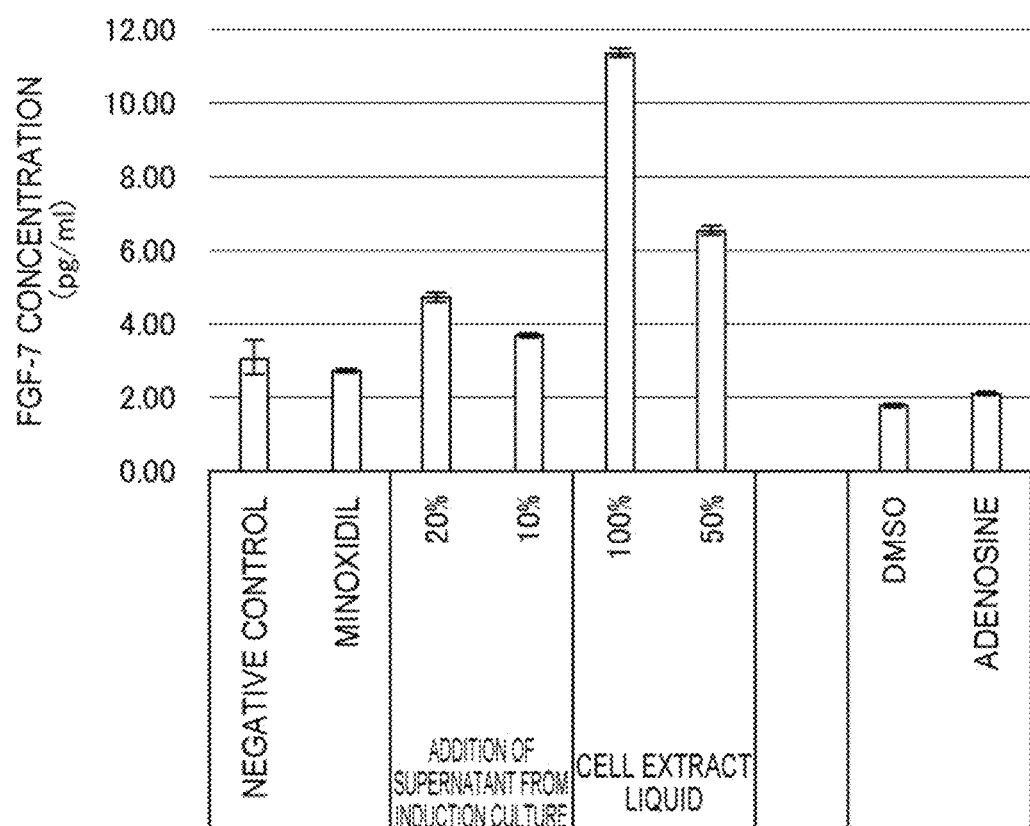
FIG. 8 is a graph that shows the results of an FGF-7 production test in hair papilla cells, according to Example 7.

After culture medium was exchanged, the hair papilla cells were cultured for 3 days and the culture medium supernatant was recovered and stored at −80° C. The culture medium supernatant was then thawed and the fibroblast growth factor 7 (FGF-7) concentration in the culture medium supernatant was measured using an FGF-7 Human ELISA kit (Cat. No. ab100519, Abcam). The results are shown in FIG. 8 and FIG. 9. It was shown that FGF-7 production by the hair papilla cells was promoted by the supernatant from culture medium used during iPS cell induction culture and by the iPS cell extract liquid. This suggested that supernatant from a culture medium used during iPS cell induction culture and an iPS cell extract liquid are effective for hair restoration, hair formation, and hair growth.

Example 8: Test of Fibroblast Migration Activity

Adult-derived normal human fibroblasts were suspended in 10% FBS culture medium to provide a concentration of $1\times10^5$ to $2\times10^5$ cells/well and were seeded to the plate of a kit (Radius Cell Migration Assay, registered trademark) for measurement of migration activity. The human fibroblasts were then treated for 2 hours with 10 µg/mL mitomycin C (Cat. No. 20898-21, Nacalai Tesque) to stop cell divisions of the human fibroblasts. The human fibroblasts were subsequently cultured for 1 day in a $CO_2$ incubator (5% $CO_2$, 37° C.).

The culture medium in some plates was exchanged to a culture medium provided by the addition, to 10% FBS culture medium, of the iPS cell extract liquid according to Example 3 to a concentration of 10 v/v %. In addition, the culture medium in some plates was exchanged to a culture medium provided by the addition, to 10% FBS culture medium, of the reprogramming culture medium supernatant according to Example 1 so as to provide a concentration of 10.0 v/v % or 20.0 v/v %.

For the negative control, the growth culture medium B on some plates was exchanged to an epidermal cell culture medium that had not been supplemented with growth additives (non-supplemented test culture medium B).

A migration test was performed by treating the human fibroblasts based on the protocol. During the course of wound healing, human fibroblasts migrate toward the wound, resulting in wound constriction. In the present example, a plate reader was used to analyze whether or not the human fibroblasts had migrated to the region blocked by the stopper prior to the migration test, where human fibroblasts were not attached. Specifically, after 23 hours after culture medium exchange, the epidermal cells were stained with Hechest and observed.

Figure 10:
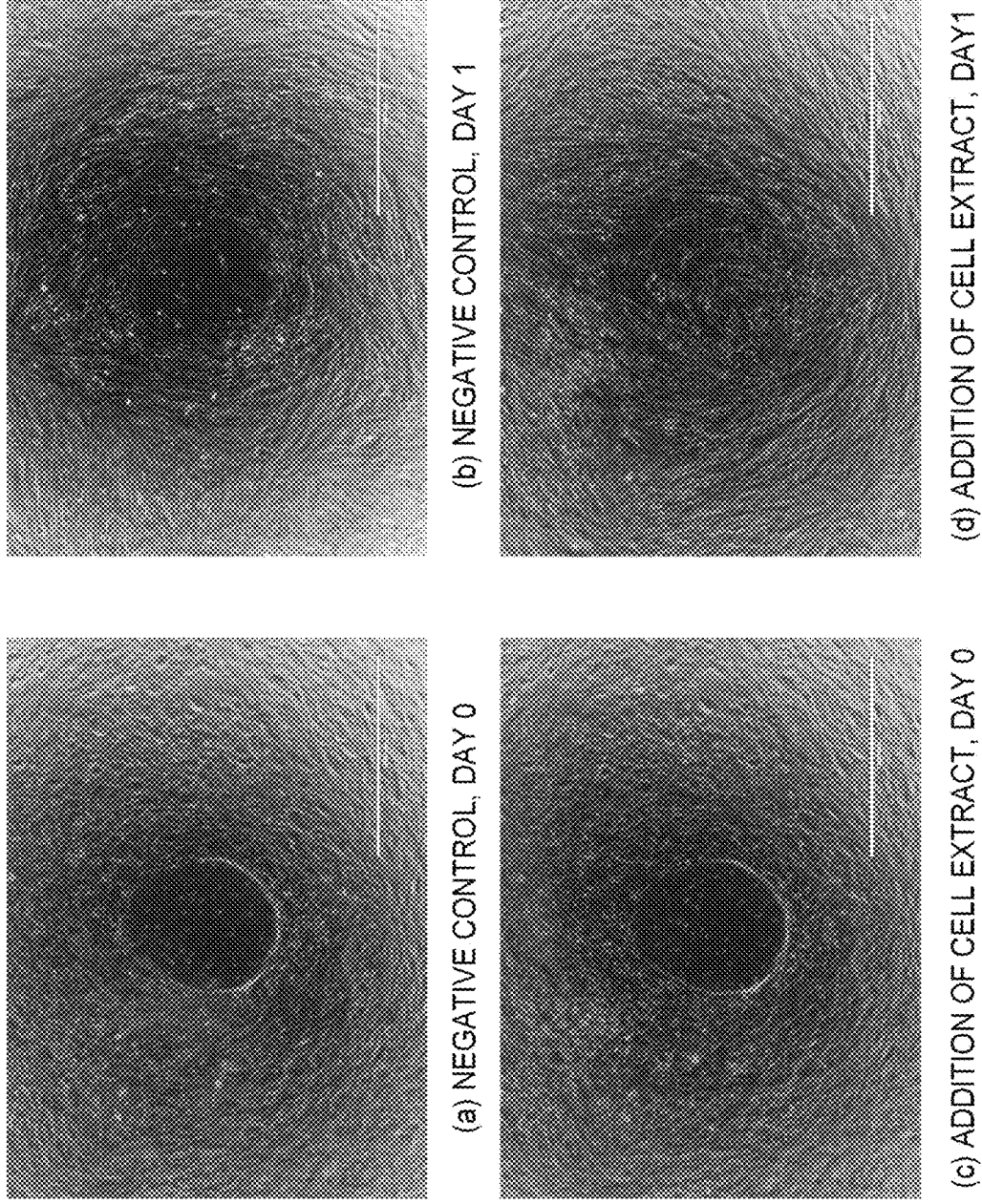
FIG. 10 is a photograph that shows the results of a fibroblast migration activity test according to Example 8.
Figure 11:
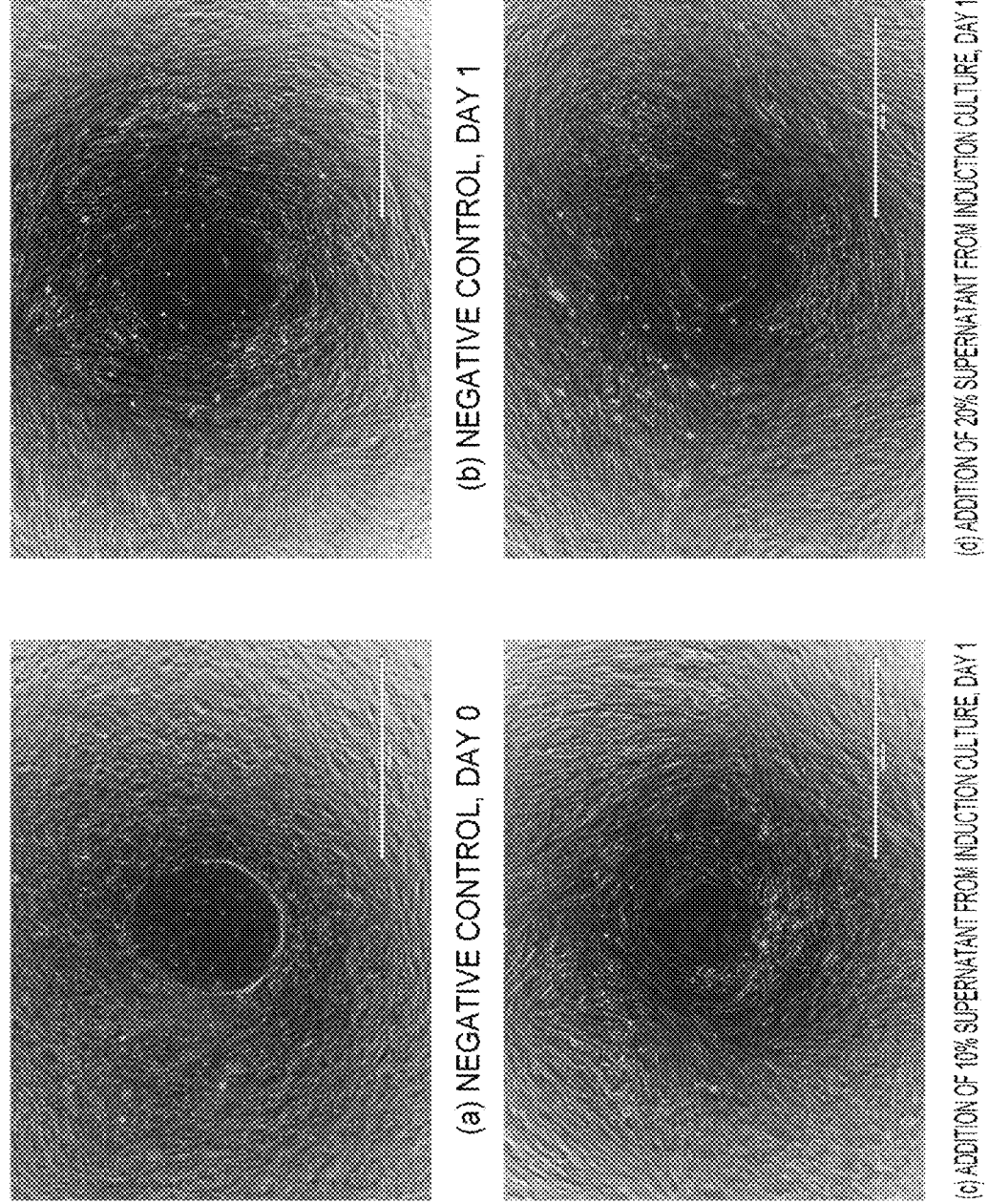
FIG. 11 is a photograph that shows the results of the fibroblast migration activity test according to Example 8.

The results are shown in FIG. 10 and FIG. 11. It was confirmed that the migration capacity of human fibroblasts is promoted by the iPS cell extract liquid and by the supernatant from a culture medium used during iPS cell induction culture. The iPS cell extract liquid and supernatant from a culture medium used during iPS cell induction culture were thus shown to be effective for wound healing.

Example 9: Preparation of Cells Derived from Accelerated Aging Disease Patients

Fibroblasts derived from a Werner syndrome patient (AG04110), fibroblasts derived from xeroderma pigmentosum patients (GM16684 and GM16687), and fibroblasts derived from a Cockayne syndrome patient (GM01098) were purchased from the Coriell Institute for Medical Research. iPS cells were induced from the fibroblasts derived from these accelerated aging patients. In addition, the iPS cells were induced to differentiate into skin fibroblasts.

Example 10: Test of UV Exposure of Skin Fibroblasts

Adult-derived normal human skin fibroblasts and the skin fibroblasts prepared in Example 9 by induction from somatic cells from accelerated aging patients were each suspended in test culture medium A at a concentration of $2\times10^5$ cells/well and were seeded to 6-well plates and were incubated for 1 day in a $CO_2$ incubator (5% $CO_2$, 37° C.).

On the following day, the skin fibroblasts in each well were exposed to ultraviolet radiation at 302 nm for 15 minutes using a UV irradiation device. The supernatant solution according to Reference Example 1 and test culture medium A were then mixed at a volume ratio of 10.00:90.00 to obtain a culture medium A supplemented with supernatant according to Reference Example 1 at a concentration of 10.00 v/v %. The test culture medium A in some of the wells was exchanged to the culture medium A supplemented with supernatant according to Reference Example 1. On the following day, all of the cells were detached from the wells using trypsin; the cells were stained with 7-aminoactinomycin D (7-AAD); and the cell mortality rate was measured using a flow cytometer.

Figure 12:
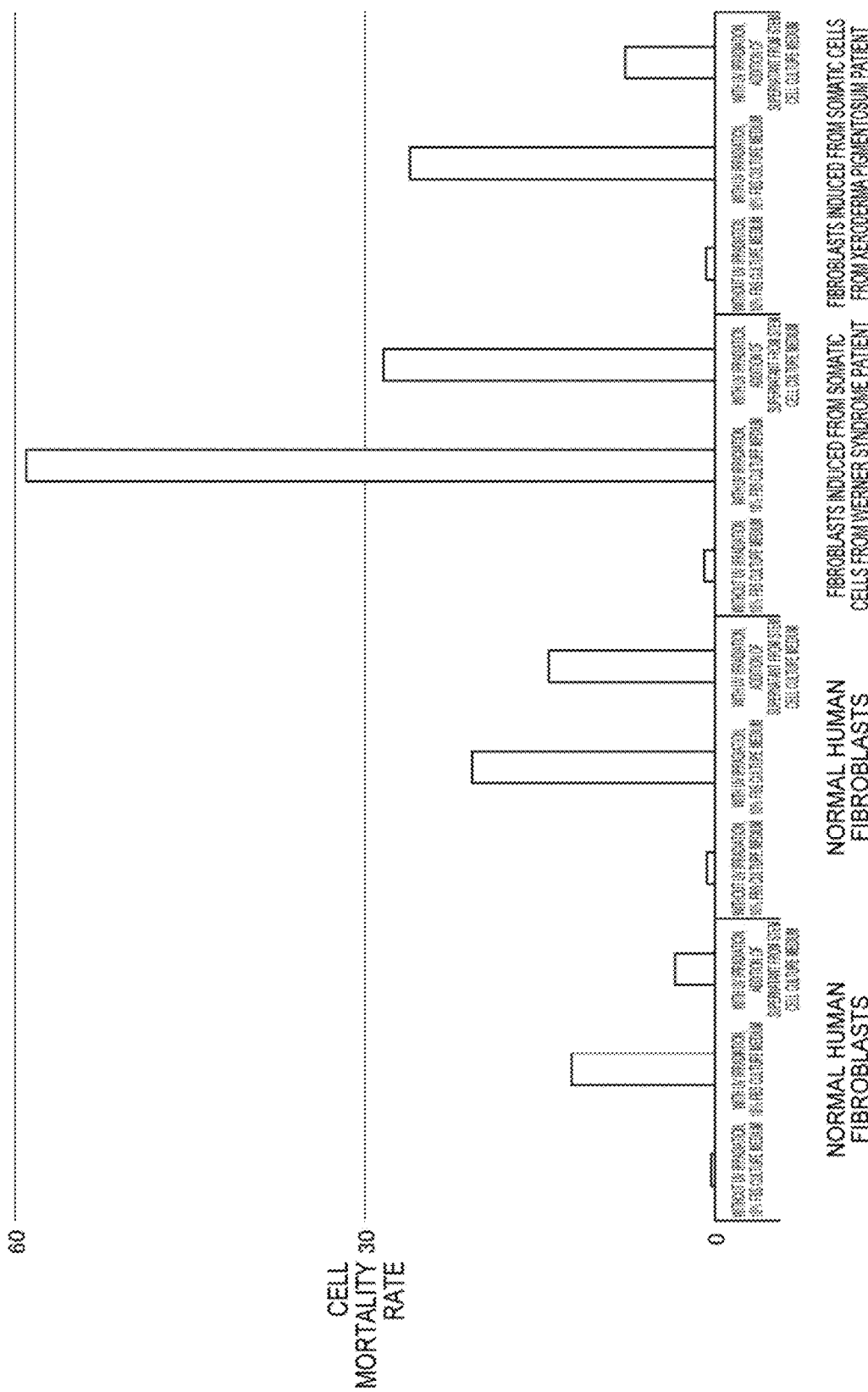
FIG. 12 is a graph that shows the results of a UV irradiation test with skin fibroblasts, according to Example 10.

According to the results shown in FIG. 12, for all of the skin fibroblasts, the UV-irradiated cells had an increased cell mortality rate over that for cells not subjected to UV irradiation. In addition, the skin fibroblasts induced from the somatic cells of accelerated aging patients had higher UV radiation-induced mortality rates than the normal skin fibroblasts. However, the skin fibroblasts in culture medium supplemented with supernatant from culture medium used during the maintenance culture of iPS cells had a higher survival rate than the skin fibroblasts in culture medium not supplemented with supernatant from culture medium used during the maintenance culture of iPS cells. This therefore suggested that skin fibroblasts induced from somatic cells from accelerated aging patients are vulnerable to UV irradiation and are suitable for screening for anti-UV substances.

Example 11: Drying Stimulation Test of Skin Fibroblasts

Each of the following were cultured for 1 day using test culture medium A in a manner similar to Example 10: the skin fibroblasts induced from somatic cells from accelerated aging patients, as prepared in Example 9, and adult-derived normal human skin fibroblasts. On the following day, each well was dried for 40 seconds in the vent opening of a clean bench. The test culture medium A in some of the wells was then exchanged to culture medium A supplemented with supernatant according to Reference Example 1. In addition, the supernatant solution according to Example 1 and test culture medium A were mixed at a volume ratio of 10.00:90.00 to provide a culture medium A supplemented with the supernatant according to Example 1 at a concentration of 10.00 v/v %. The test culture medium A in some of the wells was exchanged to the culture medium A supplemented with the supernatant according to Example 1. On the following day, all of the cells were detached from the wells using trypsin; the cells were stained with 7-aminoactinomycin D (7-AAD); and the cell mortality rate was then measured using a flow cytometer.

Figure 13:
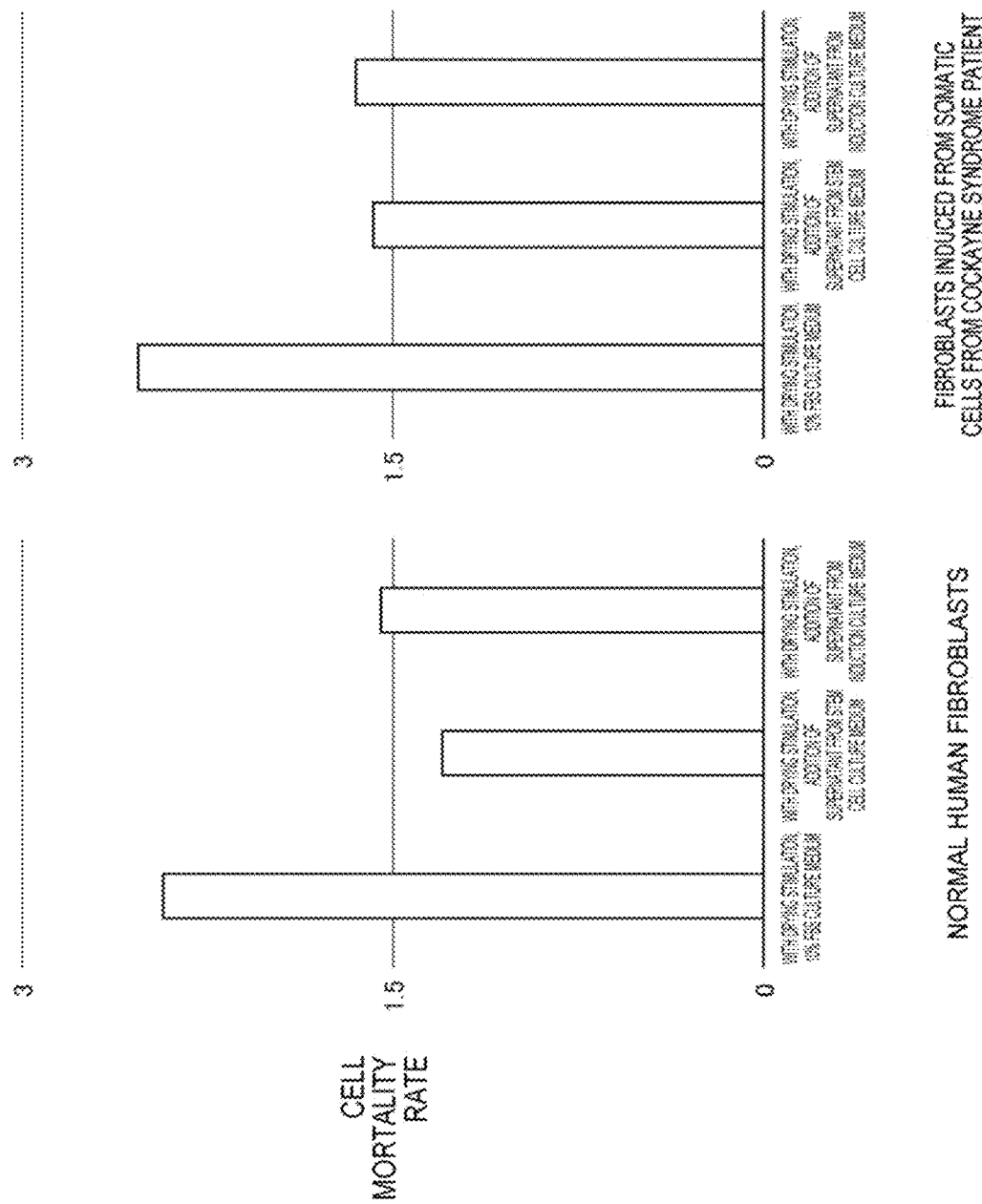
FIG. 13 is a graph that shows the results of a drying stimulation test with skin fibroblasts, according to Example 11.

According to the results shown in FIG. 13, the skin fibroblasts induced from the somatic cells of accelerated aging patients had higher drying stimulation-induced mortality rates than the normal skin fibroblasts. However, the skin fibroblasts in culture medium supplemented with supernatant from culture medium used during the maintenance culture of iPS cells had a higher survival rate than the skin fibroblasts in culture medium not supplemented with supernatant from culture medium used during the maintenance culture of iPS cells. In addition, the skin fibroblasts in culture medium supplemented with supernatant from culture medium used during culture that induced iPS cells from blood cells, had a higher survival rate than the fibroblasts in culture medium supplemented with supernatant from culture medium used during the maintenance culture of iPS cells. This therefore suggested that skin fibroblasts induced from somatic cells from accelerated aging patients are vulnerable to drying stimulation and are suitable for screening for anti-dryness stimulation substances.

Example 12: Oxidation Stress Test with Skin Fibroblasts

Each of the following were cultured for 1 day using test culture medium A in a manner similar to Example 10: the skin fibroblasts induced from somatic cells from accelerated aging patients, as prepared in Example 9, and adult-derived normal human skin fibroblasts. On the following day, hydrogen peroxide was added to a concentration of 0.03% to the test culture medium A in each well. After 10 minutes, the culture medium in some wells was returned to test culture medium A that did not contain hydrogen peroxide. In addition, the culture medium in some wells was exchanged to culture medium A supplemented with the supernatant according to Example 1, while the culture medium in some wells was exchanged to culture medium A supplemented with the supernatant according to Reference Example 1. The culture medium in some wells was exchanged to culture medium containing the iPS cell extract liquid according to Example 3. On the following day, all of the cells were detached from the wells using trypsin; the cells were stained with 7-aminoactinomycin D (7-AAD); and the cell mortality rate was then measured using a flow cytometer.

Figure 14:
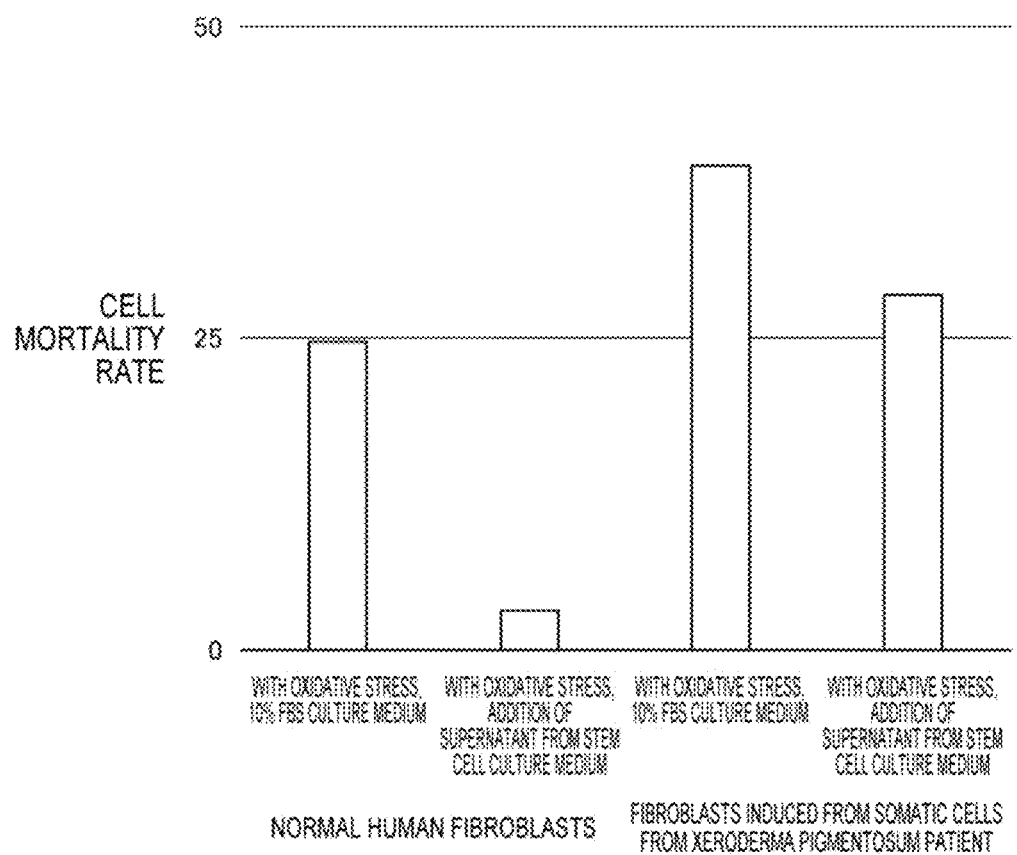
FIG. 14 is a graph that shows the results of an oxidation stress test with skin fibroblasts, according to Example 12.
Figure 15:
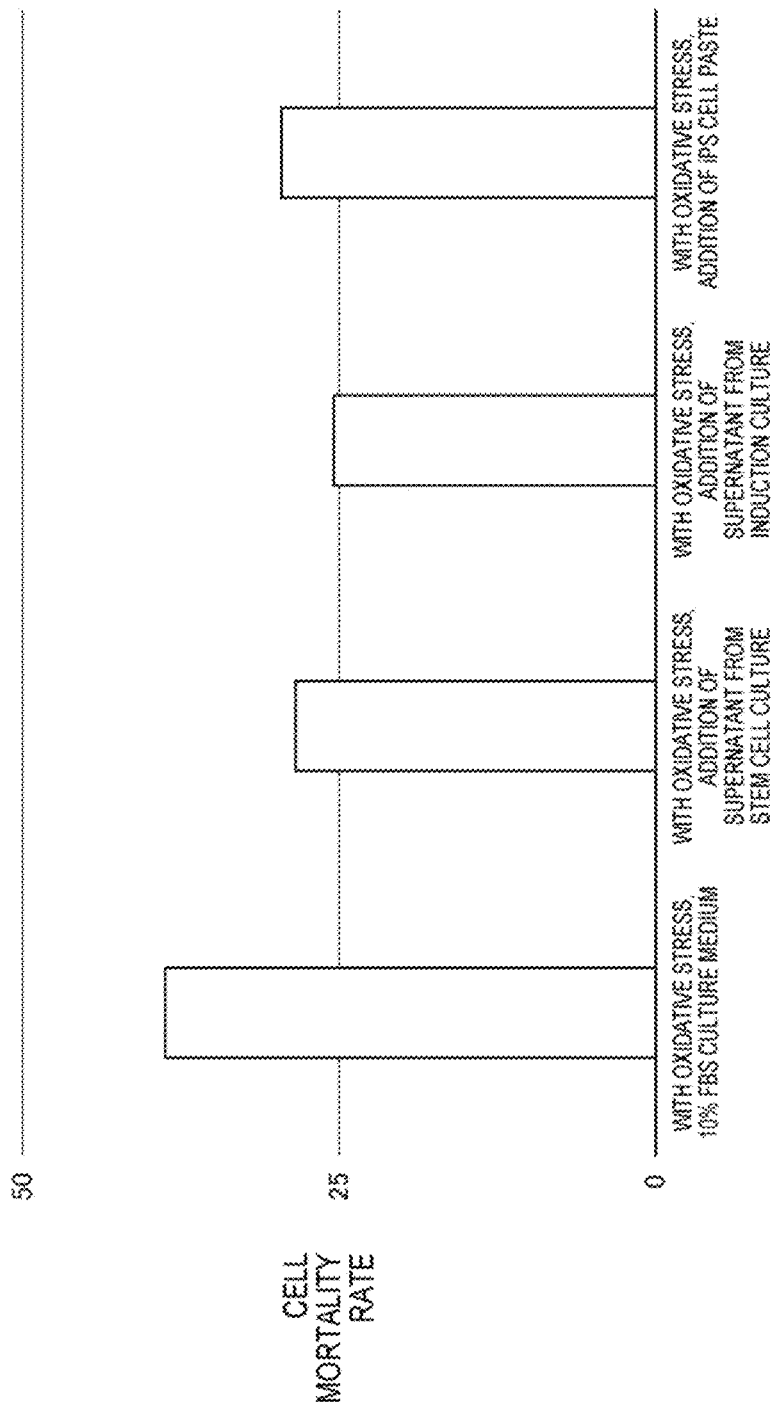
FIG. 15 is a graph that shows the results of an oxidation stress test with skin fibroblasts, according to Example 12.
Figure 18:
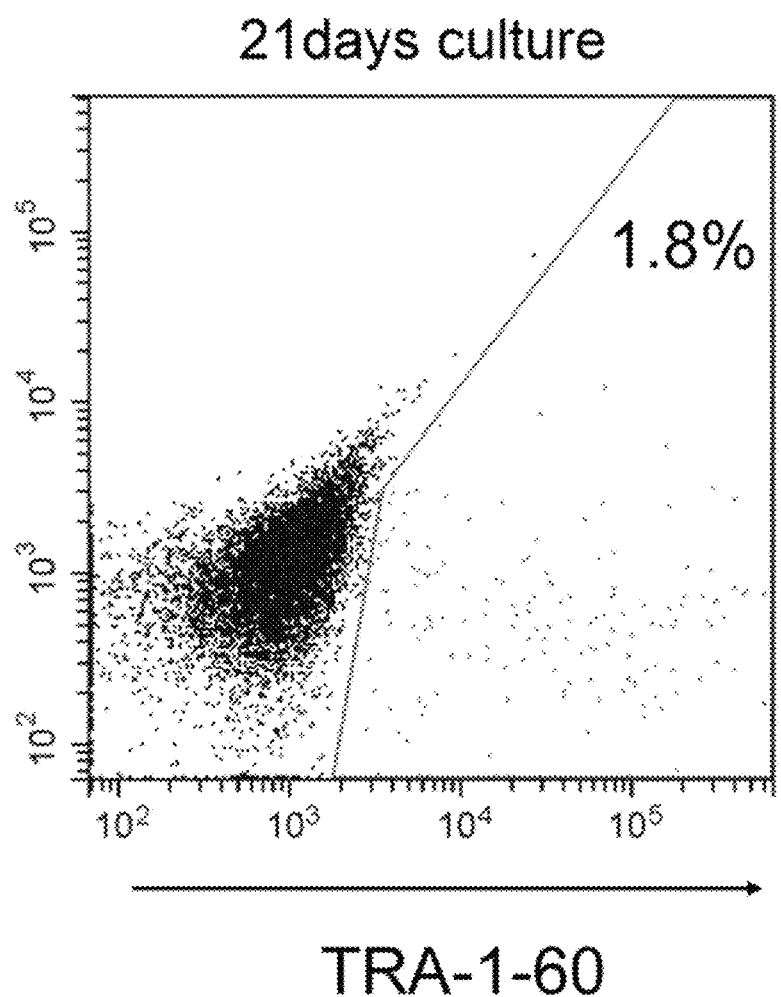
FIG. 18 is a histogram that gives the results of flow cytometry for cells according to a reference example.

According to the results as shown in FIG. 14 and FIG. 15, the skin fibroblasts induced from somatic cells from a xeroderma pigmentosum patient had a higher oxidation stress-induced mortality rate than the normal skin fibroblasts. FIG. 15 shows the cell mortality rate for skin fibroblasts induced from somatic cells from a xeroderma pigmentosum patient. As shown in FIG. 15, the skin fibroblasts in culture medium supplemented with supernatant from culture medium used during the maintenance culture of iPS cells, the skin fibroblasts in culture medium supplemented with supernatant from culture medium used during culture to induce iPS cells from blood cells, and the skin fibroblasts in culture medium supplemented with iPS cell extract liquid had higher survival rates than the skin fibroblasts in non-supplemented test culture medium A. This therefore suggested that skin fibroblasts induced from somatic cells from a xeroderma pigmentosum patient are vulnerable to oxidation stress and are suitable for screening for anti-oxidation stress substances.

Reference Example

Human iPS cells were cultured based on the examples described in Patent Publication JP-A-2016-128396. Thus, using the same stem cell culture medium as in Example 1, human iPS cells were adhesion maintenance cultured on feeder cells on an adhesion culture dish. The human iPS cells were passaged once per week. At the passage, the human iPS cells were treated with a releasing solution containing 0.25% trypsin, 0.1 mg/mL collagenase IV, 1 mmol/L $CaCl_2$, and 20% KSR.

The thusly cultured human iPS cells were detached from the adhesion culture dish using an ES cell dissociation solution (TrypLE Select, registered trademark, ThermoFisher). The detached human iPS cells were suspension cultured for 1 week in nongelled human iPS cells introduced into a nonadhesion culture dish. Embryoid bodies (EB) were formed as a result. The resulting embryoid bodies were seeded to an adhesion culture dish and were grown for 1 week (outgrowth) on DMEM that contained 10% FBS and 1% AntiAnti (registered trademark, antifungal agent).

The cells were then detached from the adhesion culture dish using a 0.05% trypsin-EDTA solution, and the cells, now divided into single cells, were seeded to a new adhesion culture dish. The cells were then cultured for 1 week using DMEM containing 10% FBS as the culture medium.

The cells were observed after confirming that the cells had reached a confluence of at least 70% to 80%. A photograph of the cells cultured in this reference example is shown in FIG. 16(a). The state of undifferentiated iPS cells is generally as in the photograph given in FIG. 16(b). The cells cultured in this reference example were thus observed, from a morphological perspective, to have not maintained an undifferentiated state. In addition, after the cells according to this reference example had been cultured for 21 days, the cells were treated with a fluorescent reagent-labeled anti-OCT3/4 antibody and a fluorescent reagent-labeled anti-NANOG antibody and the cells were then observed with a microscope to give the results in FIG. 17. FIG. 17(a) shows a photograph of the cells without the use of excitation light. FIG. 17(b) shows a photograph of the cells observed using excitation light for the fluorescent reagent bonded to the anti-OCT3/4 antibody. FIG. 17(c) shows a photograph of the cells observed using excitation light for the fluorescent reagent bonded to the anti-NANOG antibody. Fluorescence was not observed in FIG. 17(b) and FIG. 17(c), and it was thus confirmed that the cells were OCT3/4 negative and NANOG negative. In addition, when the cells were examined using a flow cytometer, the cultured cells were determined to be negative for the NANOG, OCT3/4, and TRA-1-60 undifferentiation markers. It was thus ascertained that the cells had not maintained an undifferentiated state and had undergone differentiation.

What is claimed is:

1. A method for activating secretion of a growth factor of hair papilla cells, comprising:
    applying to scalp or hair a supernatant of a culture medium,
    wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

2. The method of claim 1, wherein the somatic cells comprise at least one cell selected from the group consisting of a blood cell and a fibroblast.

3. A method for promoting production of a fibroblast growth factor family for hair papilla cells, comprising:
    applying to scalp or hair a supernatant of a culture medium,
    wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

4. The method of claim 3, wherein the somatic cells comprise at least one cell selected from the group consisting of a blood cell and a fibroblast.

5. A method for promoting production of a vascular endothelial cell growth factor for hair papilla cells, comprising:
    applying to scalp or hair a supernatant of a culture medium,
    wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

6. The method of claim 5, wherein the somatic cells comprise at least one cell selected from the group consisting of a blood cell and a fibroblast.

7. A method for activating secretion of IGF-1 for hair papilla cells, comprising:
    applying to scalp or hair a supernatant of a culture medium,
    wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

8. The method of claim 7, wherein the somatic cells comprise at least one cell selected from the group consisting of a blood cell and a fibroblast.

9. A method for improving growth of hair papilla cells, comprising:
    contacting the hair papilla cells with a composition, wherein the composition comprising a supernatant of a culture medium; and at least one selected from the group consisting of a buffering agent, an emulsifier, a suspending agent, a sedative, a stabilizer, a preservative, an antiseptic, a surfactant, a humectant, a thickener, a natural fat or oil, a skin whitener, a chelating agent, silicon, an antiseptic agent, and a microbicide, wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

10. A method for activating secretion of a growth factor of hair papilla cells, comprising:
applying a composition to scalp or hair, wherein the composition comprising a supernatant of a culture medium; and at least one selected from the group consisting of a buffering agent, an emulsifier, a suspending agent, a sedative, a stabilizer, a preservative, an antiseptic, a surfactant, a humectant, a thickener, a natural fat or oil, a skin whitener, a chelating agent, silicon, an antiseptic agent, and a microbicide, wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

11. A method for promoting production of a fibroblast growth factor family for hair papilla cells, comprising:
applying a composition, wherein the composition comprising a supernatant of a culture medium; and at least one selected from the group consisting of a buffering agent, an emulsifier, a suspending agent, a sedative, a stabilizer, a preservative, an antiseptic, a surfactant, a humectant, a thickener, a natural fat or oil, a skin whitener, a chelating agent, silicon, an antiseptic agent, and a microbicide, wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced to scalp or hair, wherein the composition comprising a supernatant of a culture medium; and at least one selected from the group consisting of a buffering agent, an emulsifier, a suspending agent, a sedative, a stabilizer, a preservative, an antiseptic, a surfactant, a humectant, a thickener, a natural fat or oil, a skin whitener, a chelating agent, silicon, an antiseptic agent, and a microbicide, wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

12. A method for promoting production of a vascular endothelial cell growth factor for hair papilla cells, comprising:
applying a composition to scalp or hair, wherein the composition comprising a supernatant of a culture medium; and at least one selected from the group consisting of a buffering agent, an emulsifier, a suspending agent, a sedative, a stabilizer, a preservative, an antiseptic, a surfactant, a humectant, a thickener, a natural fat or oil, a skin whitener, a chelating agent, silicon, an antiseptic agent, and a microbicide, wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced.

13. A method for activating secretion of IGF-1 for hair papilla cells, comprising:
applying a composition, wherein the composition comprising a supernatant of a culture medium; and at least one selected from the group consisting of a buffering agent, an emulsifier, a suspending agent, a sedative, a stabilizer, a preservative, an antiseptic, a surfactant, a humectant, a thickener, a natural fat or oil, a skin whitener, a chelating agent, silicon, an antiseptic agent, and a microbicide, wherein the supernatant of the culture medium is produced by a method comprising culturing somatic cells, introducing genes encoding reprogramming factors into the somatic cells to produce reprogrammed somatic cells, inducing iPS cells (induced pluripotent stem cells) from the reprogrammed somatic cells, and subsequently recovering the supernatant of the culture medium in which the iPS cells were induced to scalp or hair.

* * * * *